United States Patent
Kaur et al.

(10) Patent No.: US 10,007,179 B2
(45) Date of Patent: Jun. 26, 2018

(54) THERMAL ACID GENERATORS AND PHOTORESIST PATTERN TRIMMING COMPOSITIONS AND METHODS

(71) Applicant: Rohm and Haas Electronic Materials LLC, Marlborough, MA (US)

(72) Inventors: Irvinder Kaur, Northborough, MA (US); Cong Liu, Shrewsbury, MA (US); Kevin Rowell, Brighton, MA (US); Gerhard Pohlers, Needham, MA (US); Mingqi Li, Shrewsbury, MA (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 0 days. days.

(21) Appl. No.: 15/297,556

(22) Filed: Oct. 19, 2016

(65) Prior Publication Data
US 2017/0123314 A1    May 4, 2017

Related U.S. Application Data

(60) Provisional application No. 62/249,258, filed on Oct. 31, 2015.

(51) Int. Cl.
*G03F 7/11*    (2006.01)
*G03F 7/004*   (2006.01)
(Continued)

(52) U.S. Cl.
CPC .......... *G03F 7/0045* (2013.01); *C07C 309/58* (2013.01); *C07D 213/61* (2013.01);
(Continued)

(58) Field of Classification Search
CPC ... G03F 7/004; G03F 7/11; G03F 7/32; G03F 7/40; G03F 7/20; G03F 7/0397;
(Continued)

(56) References Cited

U.S. PATENT DOCUMENTS

6,180,320 B1    1/2001   Saito et al.
6,492,075 B1    12/2002  Templeton et al.
(Continued)

FOREIGN PATENT DOCUMENTS

CN    1531018 A       9/2004
JP    2002006512 A    1/2002
(Continued)

OTHER PUBLICATIONS

Machine translation of JP 2016-210732 (no date).*
(Continued)

*Primary Examiner* — Amanda C Walke
(74) *Attorney, Agent, or Firm* — Jonathan D. Baskin

(57) ABSTRACT

Provided are ionic thermal acid generators comprising an anion of an aromatic sulfonic acid comprising one or more fluorinated alcohol group and a cation. Also provided are photoresist pattern trimming compositions that include an ionic thermal acid generator, a matrix polymer and a solvent, and methods of trimming a photoresist pattern using the trimming compositions. The thermal acid generators, compositions and methods find particular applicability in the manufacture of semiconductor devices.

18 Claims, 1 Drawing Sheet

(51) Int. Cl.
| | |
|---|---|
| *C07D 213/61* | (2006.01) |
| *C07D 239/26* | (2006.01) |
| *C07C 309/58* | (2006.01) |
| *G03F 7/039* | (2006.01) |
| *G03F 7/16* | (2006.01) |
| *G03F 7/20* | (2006.01) |
| *G03F 7/32* | (2006.01) |
| *G03F 7/40* | (2006.01) |
| *G03F 7/38* | (2006.01) |
| *C07C 309/01* | (2006.01) |
| *C07C 309/33* | (2006.01) |
| *C07C 309/39* | (2006.01) |
| *C07C 309/40* | (2006.01) |
| *C07C 309/28* | (2006.01) |

(52) U.S. Cl.
CPC ......... *C07D 239/26* (2013.01); *G03F 7/0397* (2013.01); *G03F 7/11* (2013.01); *G03F 7/162* (2013.01); *G03F 7/168* (2013.01); *G03F 7/2006* (2013.01); *G03F 7/2022* (2013.01); *G03F 7/327* (2013.01); *G03F 7/38* (2013.01); *G03F 7/40* (2013.01); *C07C 309/01* (2013.01); *C07C 309/28* (2013.01); *C07C 309/33* (2013.01); *C07C 309/39* (2013.01); *C07C 309/40* (2013.01); *C07C 2603/74* (2017.05)

(58) Field of Classification Search
CPC ....... G03F 7/2022; G03F 7/38; C07C 309/01; C07C 309/28; C07C 309/33; C07C 309/39; C07C 309/40
USPC ................................................ 560/9; 562/30
See application file for complete search history.

(56) References Cited

U.S. PATENT DOCUMENTS

| | | | |
|---|---|---|---|
| 7,338,750 | B2 | 3/2008 | Kozawa et al. |
| 9,696,629 | B2* | 7/2017 | Kaur .......................... G03F 7/42 |
| 2003/0017711 | A1 | 1/2003 | Mahorowala et al. |
| 2003/0138736 | A1* | 7/2003 | Nitta .......................... G03F 7/38 430/326 |
| 2009/0311490 | A1 | 12/2009 | Burns et al. |
| 2010/0209827 | A1 | 8/2010 | Ohashi et al. |
| 2013/0171574 | A1 | 7/2013 | Xu |
| 2013/0171825 | A1* | 7/2013 | Xu ...................... H01L 21/0274 438/694 |
| 2014/0186772 | A1* | 7/2014 | Pohlers .................. G03F 7/0397 430/311 |
| 2015/0185620 | A1* | 7/2015 | Liu .......................... G03F 7/0392 430/319 |
| 2015/0212414 | A1 | 7/2015 | Pohlers et al. |
| 2016/0187783 | A1 | 6/2016 | Kaur et al. |
| 2017/0123313 | A1* | 5/2017 | Kaur ..................... G03F 7/0045 |

FOREIGN PATENT DOCUMENTS

| | | | |
|---|---|---|---|
| JP | 2002299202 | A | 10/2002 |
| JP | 2003277347 | A * | 10/2003 |
| JP | 04329216 | B2 | 9/2009 |
| JP | 2013218191 | A | 10/2013 |
| JP | 2016210732 | A * | 12/2016 |

OTHER PUBLICATIONS

Co-pending U.S. Appl. No. 15/297,545, filed Oct. 19, 2016.
Search report for corresponding China Application No. 201610917113.7 dated Nov. 14, 2017.

* cited by examiner

THERMAL ACID GENERATORS AND PHOTORESIST PATTERN TRIMMING COMPOSITIONS AND METHODS

BACKGROUND

The invention relates generally to the manufacture of electronic devices. More specifically, this invention relates to compositions and methods for trimming photoresist patterns useful in the formation of fine lithographic patterns.

In the semiconductor manufacturing industry, photoresist materials are used for transferring an image to one or more underlying layer, such as metal, semiconductor and dielectric layers, disposed on a semiconductor substrate, as well as to the substrate itself. Photoresist materials further find use, for example, in semiconductor manufacturing in the formation of ion implantation masks. To increase the integration density of semiconductor devices and allow for the formation of structures having dimensions in the nanometer range, photoresists and photolithography processing tools having high-resolution capabilities have been and continue to be developed.

Positive-tone chemically amplified photoresists are conventionally used for high-resolution processing. Such resists typically employ a resin having acid-labile leaving groups and a photoacid generator. Patternwise exposure to activating radiation through a photomask causes the acid generator to form an acid which, during post-exposure baking, causes cleavage of the acid-labile groups in exposed regions of the resin. This creates a difference in solubility characteristics between exposed and unexposed regions of the resist in an aqueous alkaline developer solution. In a positive tone development (PTD) process, exposed regions of the resist are soluble in the aqueous alkaline developer and are removed from the substrate surface, whereas unexposed regions, which are insoluble in the developer, remain after development to form a positive image.

Lithographic scaling has conventionally been achieved by increasing the numerical aperture of the optical exposure equipment and use of shorter and shorter exposure wavelengths, for example, 200 nm or less, for example, 193 nm or EUV wavelengths (e.g., 13.5 nm), with chemically amplified photoresists. To further improve lithographic performance, immersion lithography tools have been developed to effectively increase the numerical aperture (NA) of the lens of the imaging device, for example, a scanner having a KrF or ArF light source. This is accomplished by use of a relatively high refractive index fluid (i.e., an immersion fluid) between the last surface of the imaging device and the upper surface of the semiconductor wafer. The immersion fluid allows a greater amount of light to be focused into the resist layer than would occur with an air or inert gas medium. When using water as the immersion fluid, the maximum numerical aperture can be increased, for example, from 1.2 to 1.35. With such an increase in numerical aperture, it is possible to achieve a 40 nm half-pitch resolution in a single exposure process, thus allowing for improved design shrink. This standard immersion lithography process, however, is generally not suitable for manufacture of devices requiring greater resolution.

At present, the industry has reached a point at which further increases in numerical aperture or reductions in exposure wavelength are not feasible. As a result, alternative methods of scaling integrated circuit lithography are being investigated. Considerable effort has been made to extend the practical resolution beyond that achieved with standard photolithographic techniques from both a materials and processing standpoints. For example, multiple (i.e., double or higher order) patterning processes have been proposed for printing CDs and pitches beyond lower resolution limits of conventional lithographic tools. One such double patterning process is litho-litho-etch (LLE) double patterning, which involves formation of a first lithographic photoresist pattern followed by formation of a second lithographic photoresist pattern, wherein lines of the second pattern are disposed between adjacent lines of the first pattern. LLE double patterning and other advanced lithographic processes often require the formation of isolated features such as lines or posts by direct lithographic printing. The formation of isolated features with an acceptable process window, however, can pose a challenge as a result of poor aerial image contrast at defocus.

To form finer photoresist patterns than attainable by direct imaging alone, photoresist pattern trimming processes have been proposed (see, e.g., U.S. Patent Application Pub. Nos. US2013/0171574A1, US2013/0171825A1, US2014/0186772A1 and US2015/0202414A1). Photoresist trimming processes typically involve contacting a photoresist pattern that includes a polymer having acid labile groups with a composition containing an acid or acid generator. The acid or generated acid causes deprotection in a surface region of the resist pattern, which region is then removed, for example, by contact with a developer solution. The features of the resulting resist pattern are therefore reduced in size as compared with the original resist pattern.

Photoresist trimming processes can suffer from iso-dense bias, by which a difference in dimensions of isolated resist features as compared with dimensions of more densely packed resist features following the trimming process. As a result of the differing dimensions of the resist patterns and subsequently etched features, properties such as electrical characteristics of the resulting devices can be detrimentally affected. Iso-dense bias can, for example, result in a bimodal distribution of conductivity, which can also adversely impact device performance. Without wishing to be bound by any particular theory, the inventors believe that the problem is a result of an increased presence of acid in the isolated resist pattern regions available for deprotection of the resist patterns as compared with the more densely packed resist pattern regions. As such, increased deprotection of the isolated resist patterns can occur due to a larger amount of acid penetrating further into the isolated pattern surface. Iso-dense bias provides an indication of whether an existing photomask can be used to print isolated and dense patterns on the mask without the need for Optical Proximity Correction (OPC). If OPC is required, a new photomask is typically required. It would be desirable to reduce or avoid the occurrence of post-trim iso-dense bias.

There is a need in the art for thermal acid generators, trimming compositions and trimming methods useful in electronic device fabrication that address one or more problem associated with the state of the art.

SUMMARY OF THE INVENTION

In accordance with a first aspect of the invention, ionic thermal acid generators are provided. The ionic thermal acid generators comprise: an anion of an aromatic sulfonic acid comprising one or more fluorinated alcohol group; and a cation.

In accordance with a further aspect of the invention, photoresist pattern trimming compositions are provided. The compositions comprise: an ionic thermal acid generator, a matrix polymer and a solvent. The ionic thermal acid generator comprises an anion of an aromatic sulfonic acid comprising one or more fluorinated alcohol group, and a cation.

In accordance with a further aspect of the invention, methods of trimming a photoresist pattern are provided. The methods comprise: (a) providing a substrate; (b) forming a photoresist pattern on the substrate, wherein the photoresist pattern is formed from a photoresist composition comprising: a matrix polymer comprising an acid labile group; a photoacid generator; and a solvent; (c) coating a photoresist trimming composition on the substrate over the photoresist pattern, the photoresist trimming composition comprising: an ionic thermal acid generator comprising an anion of an aromatic sulfonic acid comprising one or more fluorinated alcohol group, and a cation; (d) heating the coated substrate, thereby causing a change in polarity of the photoresist matrix polymer in a surface region of the photoresist pattern; and (e) contacting the photoresist pattern with a rinsing agent to remove the surface region of the photoresist pattern, thereby forming a trimmed photoresist pattern.

The ionic thermal acid generators, photoresist pattern trimming compositions and photoresist pattern methods of the invention can produce fine lithographic patterns, with controllably reduced resist pattern dimensions. Preferred compositions and methods of the invention allow for the formation of patterns having beneficial line width roughness properties and/or for the formation of isolated patterns, for example, isolated lines or posts, with desirable iso-dense bias characteristics.

The terminology used herein is for the purpose of describing particular embodiments only and is not intended to be limiting of the invention. The singular forms "a", "an" and "the" are intended to include singular and plural forms, unless the context indicates otherwise.

Various materials and groups that are "optionally substituted" may be suitably substituted at one or more available positions. Except as otherwise specified, "substituted" shall be understood to mean including at least one substituent such as a halogen (i.e., F, Cl, Br, I), hydroxyl, amino, thiol, carboxyl, carboxylate, ester, ether, amide, nitrile, sulfide, disulfide, nitro, $C_{1-18}$ alkyl, $C_{1-18}$ alkenyl (including norbornenyl), $C_{1-18}$ alkoxyl, $C_{2-18}$ alkenoxyl (including vinyl ether), $C_{4-18}$ aryl, $C_{6-18}$ aryloxyl, $C_{7-18}$ alkylaryl, or $C_{7-18}$ alkylaryloxyl, optionally including one or more heteroatom.

"Fluorinated" shall be understood to mean having one or more fluorine atoms incorporated in the group.

As used herein, the term "alkyl" includes linear alkyl, branched alkyl, cyclic (monocyclic or polycyclic) alkyl, and alkyl groups combining two-way and three-way combinations of linear, branched, and cyclic groups.

DESCRIPTION OF THE DRAWINGS

The present invention will be described with reference to the following drawing, in which like reference numerals denote like features, and in which.

DETAILED DESCRIPTION

Figure 1A:
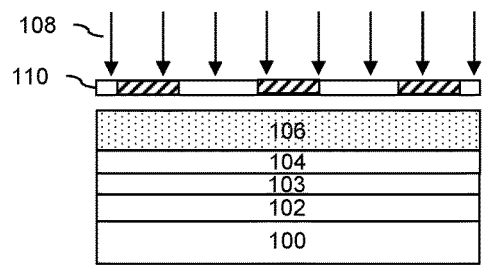
FIG. 1A-H illustrates a process flow for forming a photolithographic pattern in accordance with the invention.

Thermal Acid Generators and Photoresist Pattern Trimming Compositions

The photoresist pattern trimming compositions include a matrix polymer, an ionic thermal acid generator comprising an anion of an aromatic sulfonic acid comprising one or more fluorinated alcohol group, and a cation, and a solvent, and can include one or more optional additional component. When coated over a photoresist pattern, photoresist trimming compositions in accordance with the invention can provide fine lithographic patterns with controllably reduced resist pattern dimensions. Preferred photoresist compositions of the invention can provide favorable linewidth roughness (LWR) and/or iso-dense bias properties.

The matrix polymer allows for the compositions to be coated over the photoresist pattern in the form of a layer having a desired thickness. This will help to ensure the presence of a sufficient content of generated acid for interaction with the photoresist pattern surface. The matrix polymer should have good solubility in the rinsing solution to be used in the trimming process. For example, the matrix polymer can be soluble in an aqueous alkaline developer, preferably aqueous quaternary ammonium hydroxide solutions such as aqueous tetramethylammonium hydroxide, or in water. To minimize residue defects originated from the overcoat materials, the dissolution rate of a dried layer of the trimming composition should be greater than that of the photoresist pattern surface region to be removed by the developer solution. The matrix polymer typically exhibits a developer dissolution rate of 100 Å/second or higher, preferably 1000 Å/second or higher. The matrix polymer is soluble in the solvent of the trimming composition, described herein. The matrix polymer can be chosen, for example, from polyvinyl alcohols, polyacrylic acids, polyvinyl pyrrolidones, polyvinyl amines, polyvinyl acetals, poly(meth)acrylates and combinations thereof. Preferably, the polymer contains one or more functional group chosen from —OH, —COOH, —SO$_3$H, SiOH, hydroxyl styrene, hydroxyl naphthalene, sulfonamide, hexafluoroisopropyl alcohol, anhydrates, lactones, esters, ethers, allylamine, pyrrolidones and combinations thereof.

The content of the matrix polymer in the composition will depend, for example, on the target thickness of the layer, with a higher polymer content being used for thicker layers. The matrix polymer is typically present in the compositions in an amount of from 80 to 99 wt %, more typically from 90 to 98 wt %, based on total solids of the trimming composition. The weight average molecular weight (Mw) of the polymer is typically less than 400,000, preferably from 3000 to 50,000, more preferably from 3000 to 25,000.

Polymers useful in the overcoat compositions can be homopolymers or copolymers having a plurality of distinct repeat units, for example, two, three, four or more distinct repeat units. The trimming compositions typically include a single polymer, but can optionally include one or more additional polymer. Suitable polymers and monomers for use in the overcoat compositions are commercially available and/or can readily be made by persons skilled in the art.

The trimming compositions further include an ionic thermal acid generator (TAG) comprising an anion of an aromatic sulfonic acid comprising one or more fluorinated alcohol group, and a cation. The thermal acid generator, when heated at or above its activation temperature, generates the corresponding conjugate aromatic sulfonic acid which drives the photoresist pattern trimming process. The inventors have recognized that use of a free acid rather than a thermal acid generator in the trimming compositions can result in reduced shelf life stability of the composition due to chemical changes in the matrix polymer from premature reaction with the acid.

A typical TAG reaction scheme for thermal acid generators of the invention is shown below:

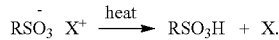

In the case of a photoresist pattern formed from a photoresist based on deprotection reaction, the generated acid can cleave the bond of acid labile groups (protected groups), such as acid labile ester groups or acetal groups, to cause deprotection and formation of acid groups in the resist polymer at the surface of the photoresist pattern.

For purposes of tuning lithographic properties such as trim amount, reducing LWR and/or improving iso-dense bias properties, the use of ionic thermal acid generators that generate slow diffusing sulfonic acids is preferred. Use of a bulky anion is preferred to render the generated acid slow diffusing. Preferred are aromatic sulfonic acids that are substituted with bulky groups. Suitable bulky groups include, for example, one or more of branched, monocyclic or polycyclic optionally substituted alkyl, preferably optionally substituted adamantyl, optionally substituted aryl, optionally substituted aralkyl and fluorinated or nonfluorinated alcohols. The generated aromatic sulfonic acid is preferably a sulfonic acid comprising an optionally substituted phenyl, biphenyl, naphthyl, anthracenyl, thiophene or furan group, or a combination thereof. A larger TAG anion molar volume is typically desired for reduced acid diffusion into the resist pattern. The molar volume of the TAG anion is preferably from 100 to 1000 cm$^3$, from 300 to 800 cm$^3$ or from 400 to 600 cm$^3$. The anions typically have a weight average molecular weight Mw of from 200 to 2000, more typically from 500 to 1000.

The presence of the one or more fluorinated alcohol group on the TAG anion can further contribute to slow diffusivity of the generated acid due to increased polar functionalities which can bind more effectively with the polymer. The fluorinated alcohol group can be partially fluorinated or completely fluorinated, i.e., perfluorinated. Preferred fluorinated alcohol groups include a fluorine atom and/or a pendant fluorinated group such as partially or completely fluorinated alkyl, typically methyl, ethyl or propyl, bonded to a carbon at the alpha position of the alcohol hydroxyl. Particularly preferred are fluoroalcohol groups of the formula —C(CF$_3$)$_2$OH. It is preferred that the fluorinated alcohol group is bonded to an aromatic ring of the TAG anion through a linking group. Use of a linking group in this manner can further add to bulkiness of the TAG anion and conjugate acid. Suitable linking groups include, for example, sulfur, optionally substituted amino groups, amides, ethers, carbonyl esters, sulfonyl esters, sulfones, sulfonamides and divalent hydrocarbon groups, for example, C1-20 linear, branched or cyclic optionally substituted hydrocarbon groups, and combinations thereof. For purposes of increasing the bulkiness of the aromatic sulfonic acid, it is preferred that the aromatic acid include a plurality of fluorinated alcohol groups and/or one or more other type of group, for example, carboxyl, hydroxyl, nitro, cyano, C1-5 alkoxy, formyl, esters, optionally substituted alkyl, C5 or higher monocyclic, polycyclic, fused polycyclic cycloaliphatic, or aryl, which may optionally comprise a heteroatom. Preferably, the TAG anion has a plurality of fluorinated alcohol groups, and more preferably, the TAG anion has a plurality of fluorinated alcohol groups that are bonded to an aromatic ring through a respective linking group.

The thermal acid generator is preferably of the following general formula (I):

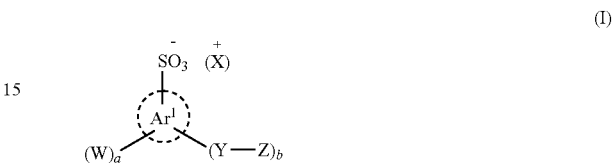

wherein: Ar$^1$ represents an optionally substituted carbocyclic or heterocyclic aromatic group. Ar$^1$ may, for example, include a single aromatic ring such as phenyl or pyridyl; an aromatic ring substituted with another aromatic group such as biphenyl; fused aromatic rings such as naphthyl, anthracenyl, pyrenyl or quinolinyl; or fused ring systems having both aromatic and non-aromatic rings such as 1,2,3,4-tetrahydronaphthalene, 9,10-dihydroanthracene, or fluorene. Optionally, the aromatic group may be substituted. The aromatic group can, for example, have one or more of its hydrogen atoms replaced with one or more substituent such as C$_{1-30}$ alkyl, C$_{2-30}$ alkenyl, C$_{7-30}$ aralkyl, C$_{6-30}$ aryl, —OR$^1$, —C$_{1-30}$ alkylene-OR$^1$, and —C$_{1-30}$ alkylidene-OR$^1$; wherein R$^1$ is selected from H, C$_{1-30}$ alkyl, C$_{2-30}$ alkenyl, and C$_{6-30}$ aryl. A wide variety of aromatic groups may be used for Ar$^1$, which may be unsubstituted or substituted. Such unsubstituted aromatic groups may have from 5 to 40 carbons, preferably from 6 to 35 carbons, and more preferably from 6 to 30 carbons. Suitable aromatic groups include, but are not limited to: phenyl, biphenyl, naphthalenyl, anthracenyl, phenanthrenyl, pyrenyl, tetracenyl, triphenylenyl, tetraphenyl, benzo[f]tetraphenyl, benzo[m]tetraphenyl, benzo[k]tetraphenyl, pentacenyl, perylenyl, benzo[a]pyrenyl, benzo[e]pyrenyl, benzo[ghi]perylenyl, coronenyl, quinolonyl, 7,8-benzoquinolinyl, fluorenyl, and 12H-dibenzo[b,h]fluorenyl, each of which may by unsubstituted or substituted; W independently represents a group chosen from carboxyl, hydroxy, nitro, cyano, C1-5 alkoxy and formyl; X is a cation as described below; Y independently represents a linking group chosen, for example, from sulfur, optionally substituted amino groups, amides, ethers, carbonyl esters, sulfonyl esters, sulfones, sulfonamides and divalent hydrocarbon group, for example, C1-20 straight chain, branched or cyclic optionally substituted hydrocarbon groups, and combinations thereof; Z independently represents a group chosen from hydroxyl, fluorinated alcohols, esters, optionally substituted alkyl, C5 or higher optionally substituted monocyclic, polycyclic, fused polycyclic cycloaliphatic, or aryl, which may optionally comprise a heteroatom, provided at least one occurrence of Z is a fluorinated alcohol group; a is an integer of 0 or greater, typically 0 to 2; b is an integer of 1 or greater, typically 1 or 2; provided that a+b is at least 1 and not greater than the total number of available aromatic carbon atoms of the aromatic group, with a+b of from 2 to 5 being typical, more typically 2 or 3.

Suitable exemplary thermal acid generator anions include, without limitation, the following:

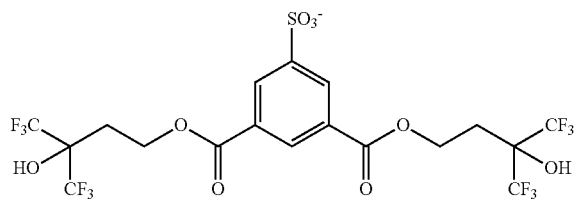
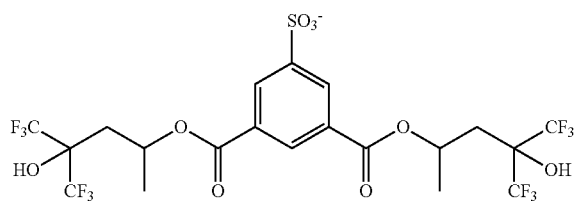
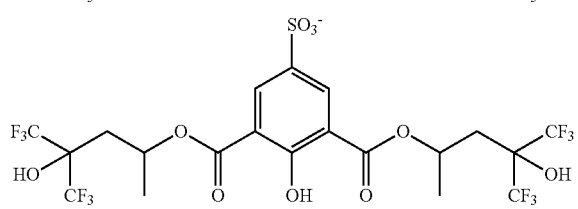
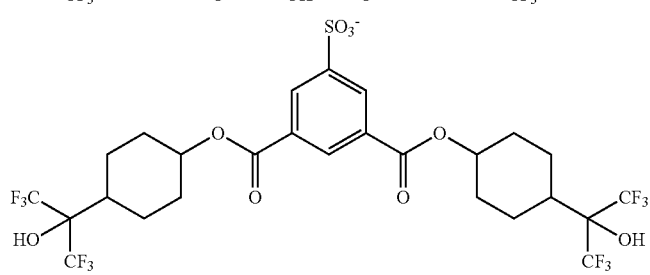
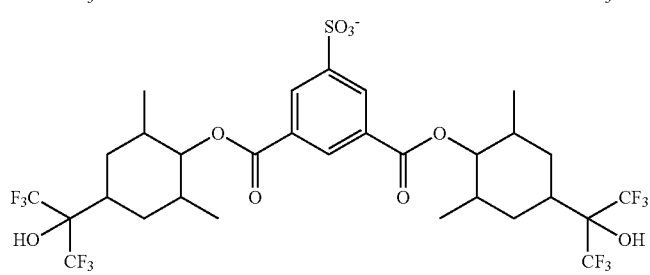
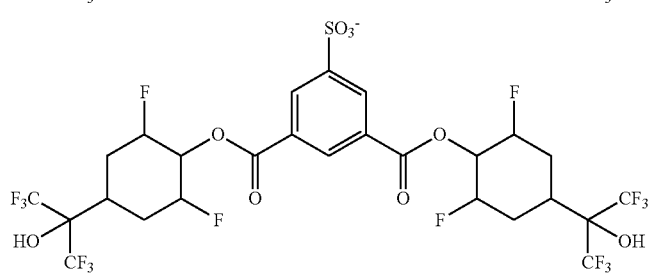
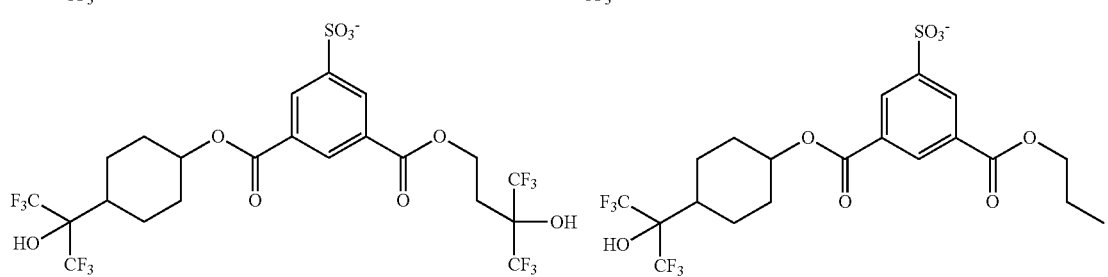

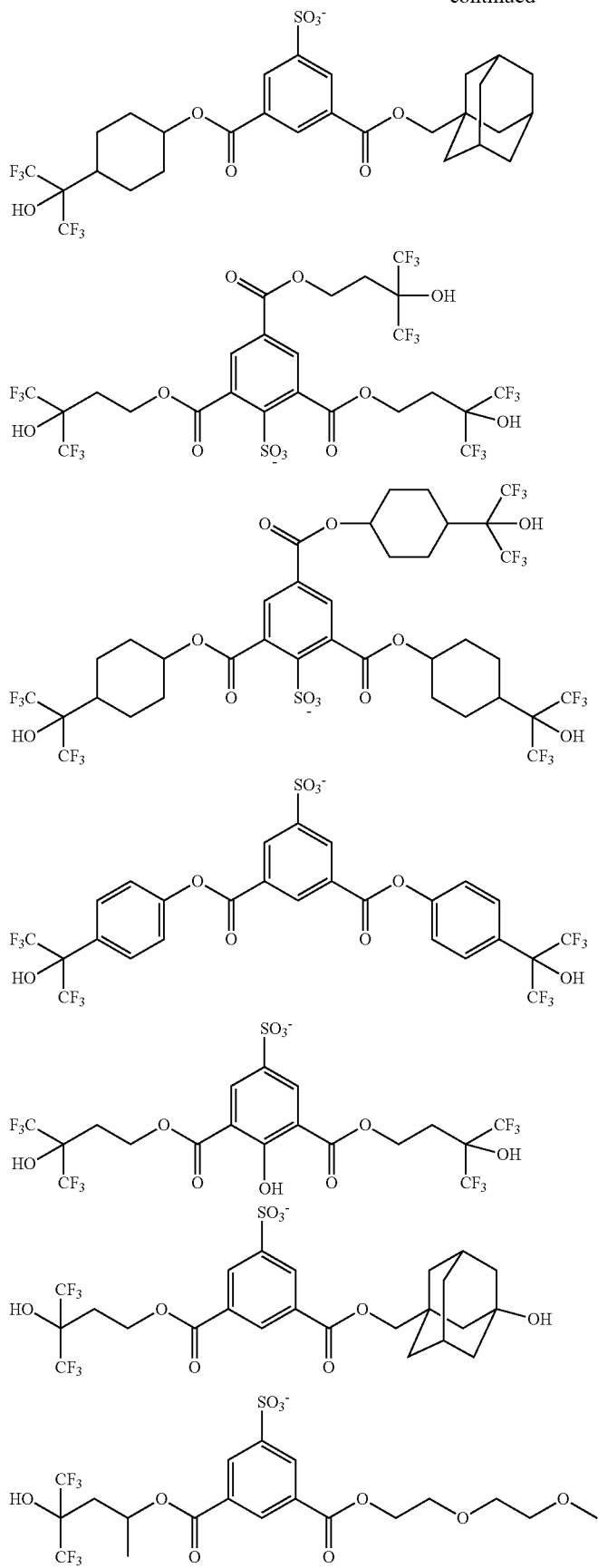

-continued
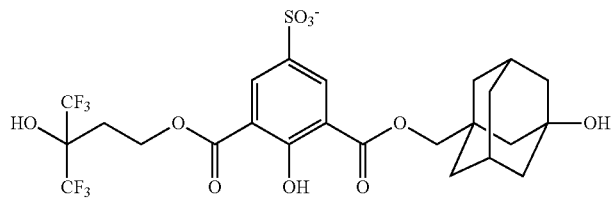
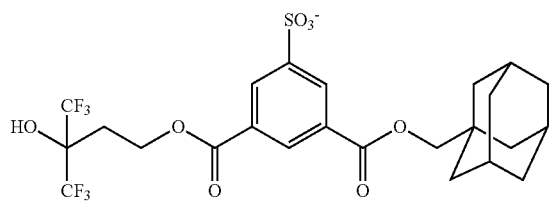
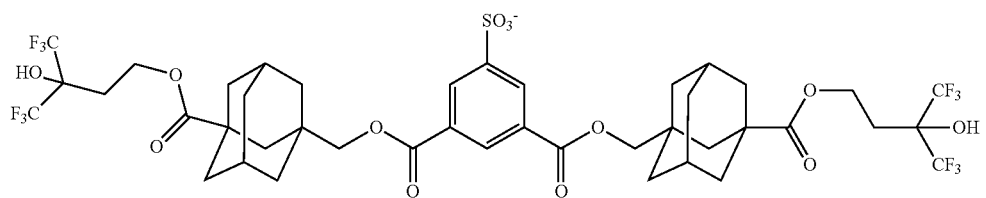
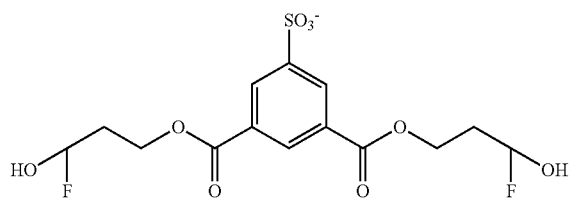
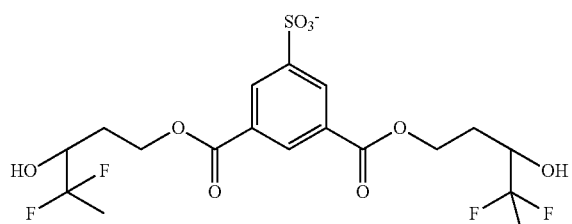
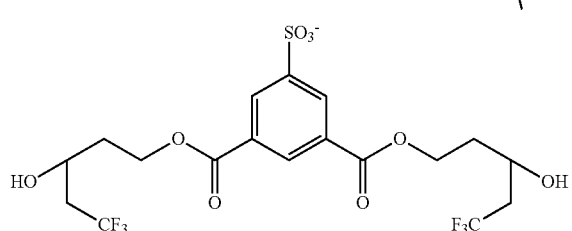
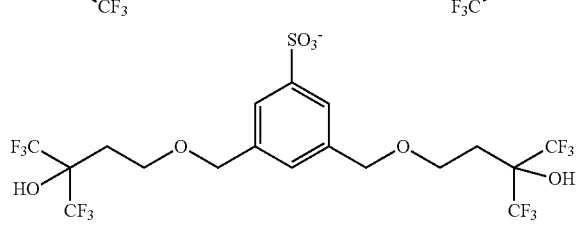
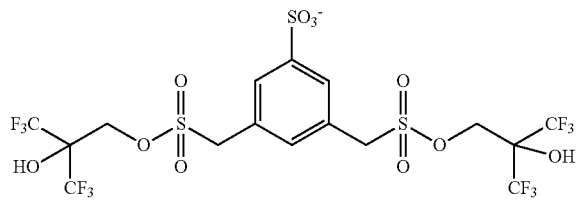

-continued
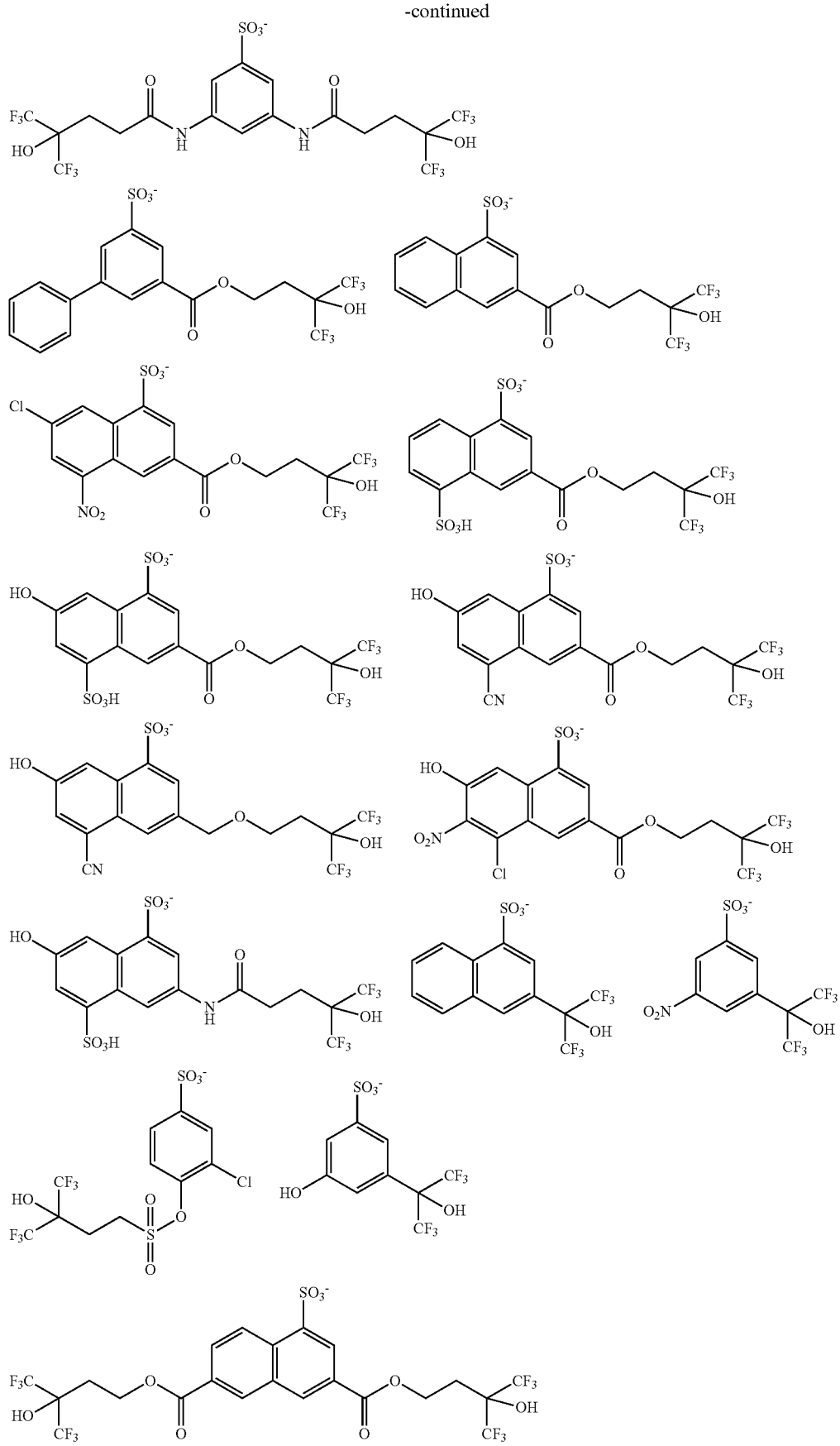

-continued
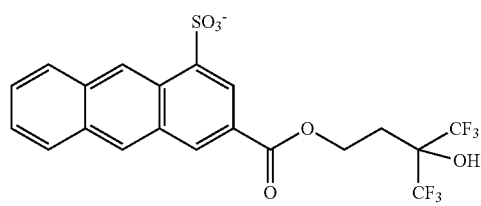
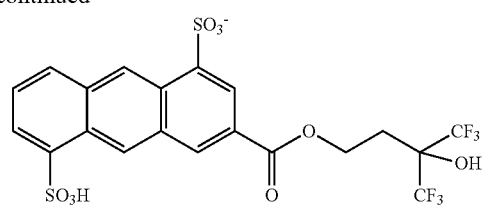
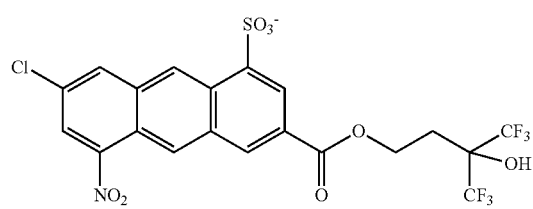
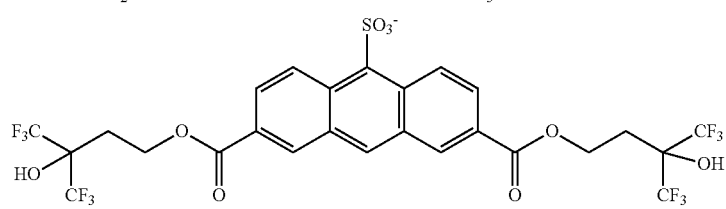
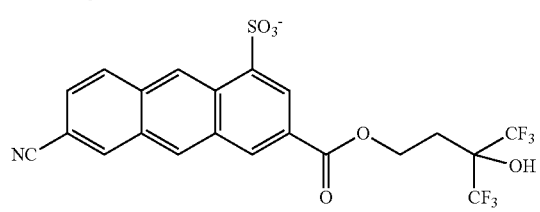
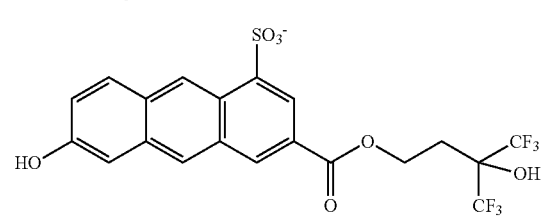
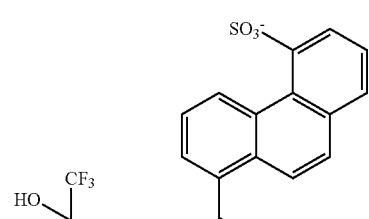
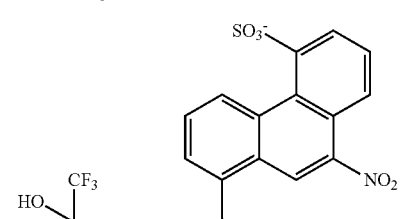
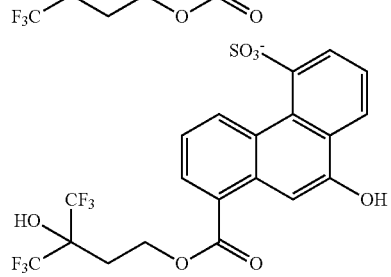
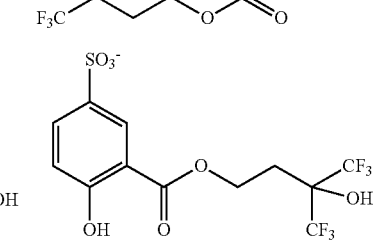
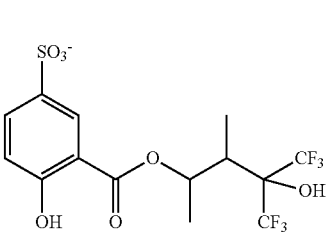
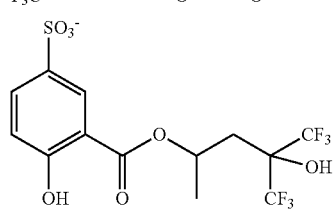
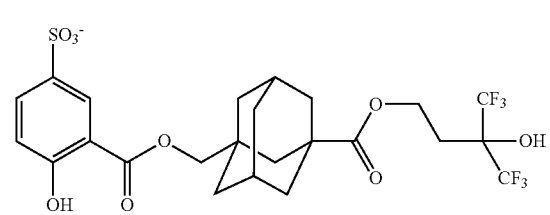
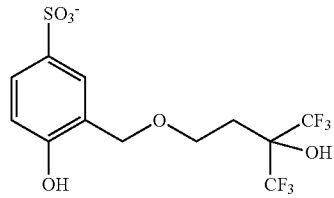
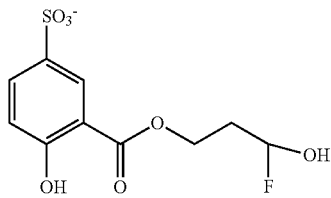
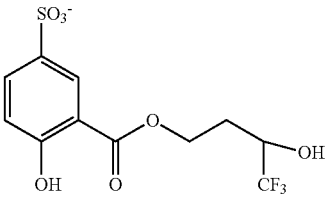

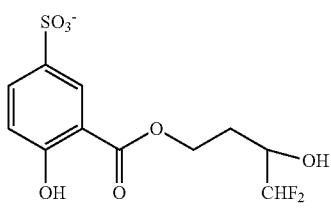
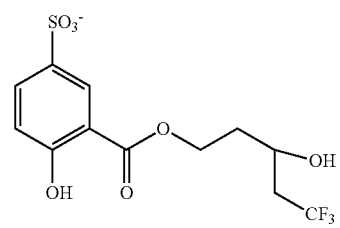
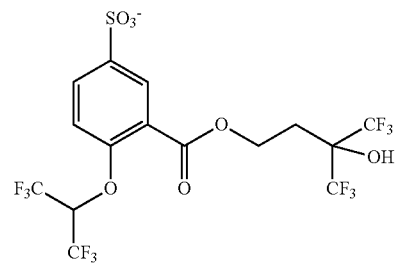
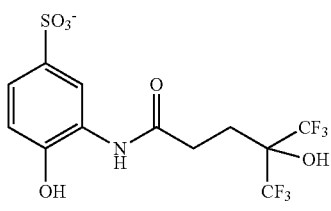
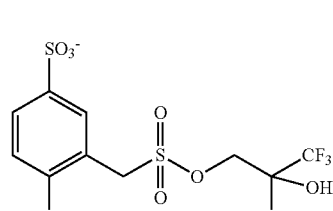
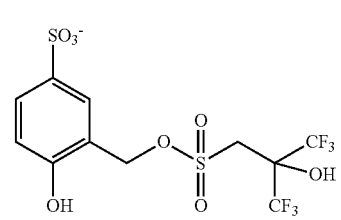
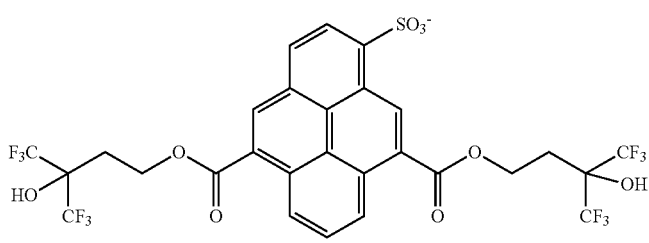
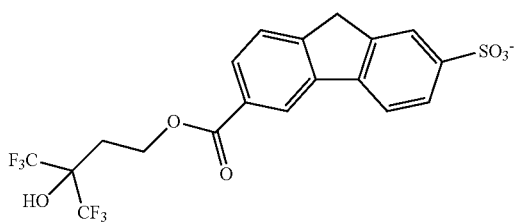
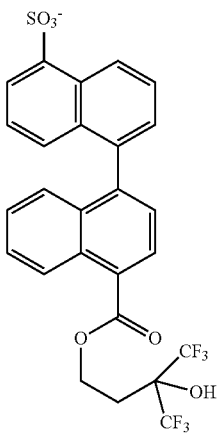
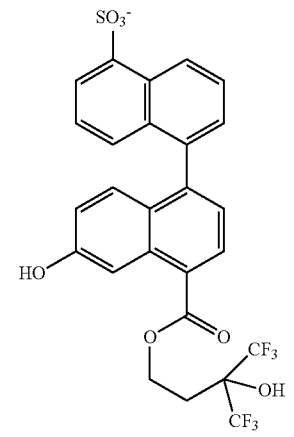

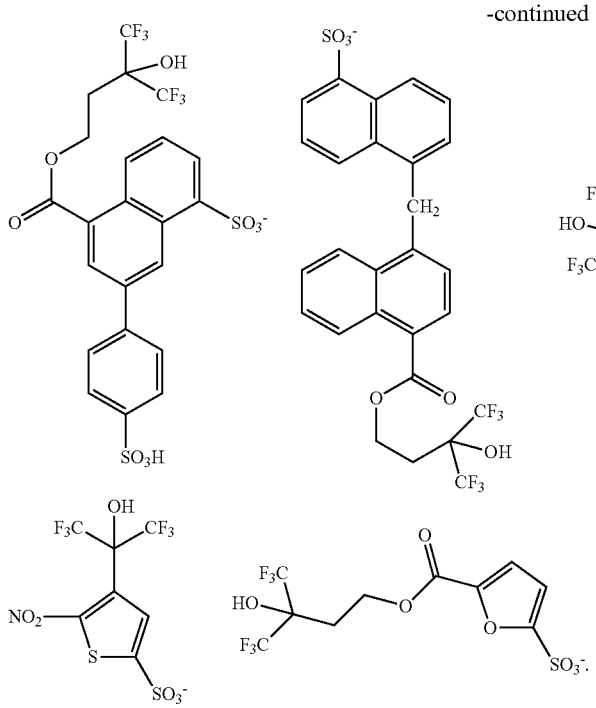

The thermal acid generator cation is preferably an organic cation. Preferably, the cation is a nitrogen-containing cation of the general formula (I):

(BH)⁺          (I)

which is the monoprotonated form of a nitrogen-containing base B. Suitable nitrogen-containing bases B include, for example: optionally substituted amines such as ammonia, difluoromethylammonia, C1-20 alkyl amines, and C3-30 aryl amines, for example, nitrogen-containing heteroaromatic bases such as pyridine or substituted pyridine (e.g., 3-fluoropyridine), pyrimidine and pyrazine; nitrogen-containing heterocyclic groups, for example, oxazole, oxazoline, or thiazoline. The foregoing nitrogen-containing bases B can be optionally substituted, for example, with one or more group chosen from alkyl, aryl, halogen atom (preferably fluorine), cyano, nitro and alkoxy. Of these, base B is preferably a heteroaromatic base.

Base B typically has a pKa from 0 to 5.0, or between 0 and 4.0, or between 0 and 3.0, or between 1.0 and 3.0. As used herein, the term "$pK_a$" is used in accordance with its art-recognized meaning, that is, $pK_a$ is the negative log (to the base 10) of the dissociation constant of the conjugate acid (BH)⁺ of the basic moiety (B) in aqueous solution at about room temperature. In certain embodiments, base B has a boiling point less than about 170° C., or less than about 160° C., 150° C., 140° C., 130° C., 120° C., 110° C., 100° C. or 90° C.

Exemplary suitable nitrogen-containing cations (BH)⁺ include $NH_4^+$, $CF_2HNH_2^+$, $CF_3CH_2NH_3^+$, $(CH_3)_3NH^+$, $(C_2H_5)_3NH^+$, $(CH_3)_2(C_2H_5)NH^+$ and the following:

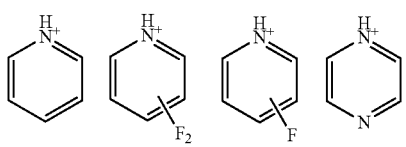

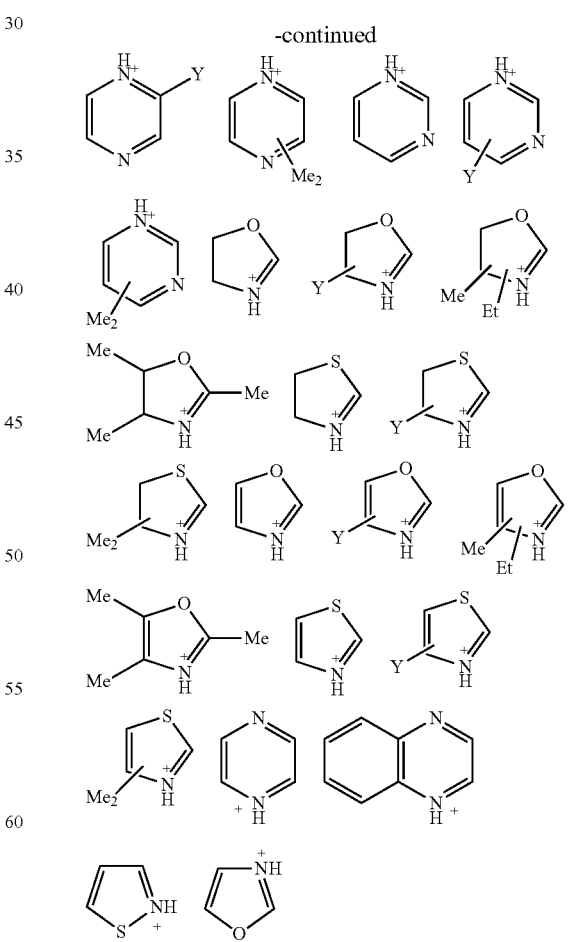

in which Y is alkyl, preferably, methyl or ethyl.

Other suitable cations include onium cations. Suitable onium cations include, for example, sulfonium and iodonium cations, for example, those of the following general formula

(II)

wherein X is S or I, wherein when X is I then a is 2, and when X is S then a is 3; $R^3$ is independently chosen from organic groups such as optionally substituted $C_{1-30}$ alkyl, polycyclic or monocyclic $C_{3-30}$ cycloalkyl, polycyclic or monocyclic $C_{6-30}$ aryl, or a combination thereof, wherein when X is S, two of the $R^3$ groups together optionally form a ring.

Exemplary suitable sulfonium and iodonium cations include the following:

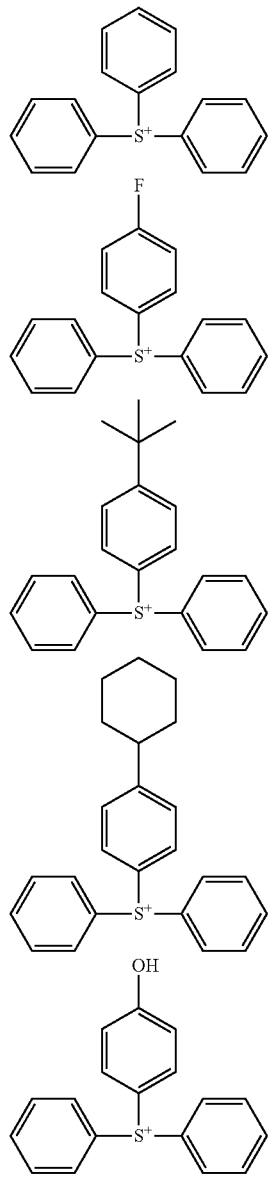

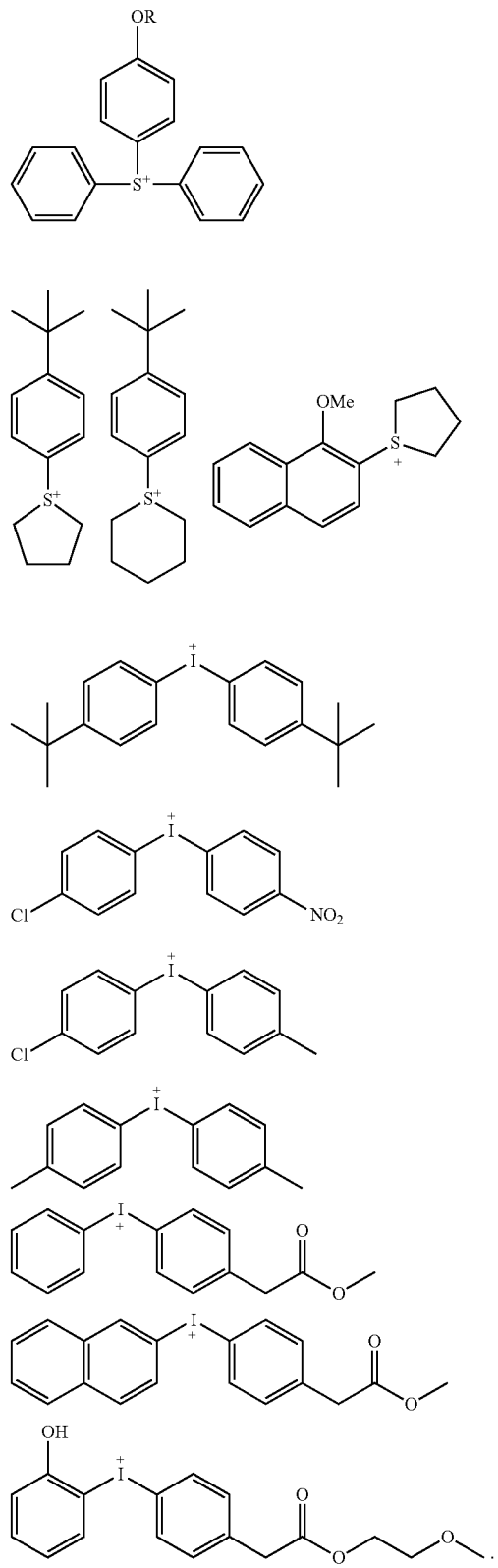

It will be appreciated that suitable TAGs in accordance with the invention include any combination of the described anions with the described cations. Exemplary suitable TAGs, without limitation include the following:

23
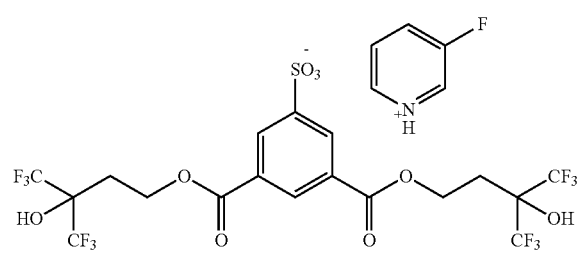
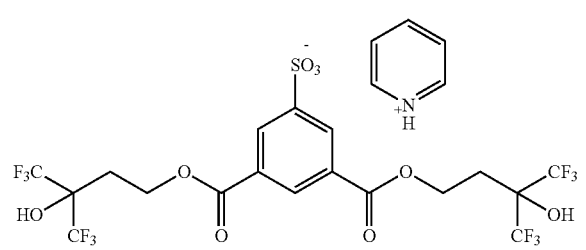
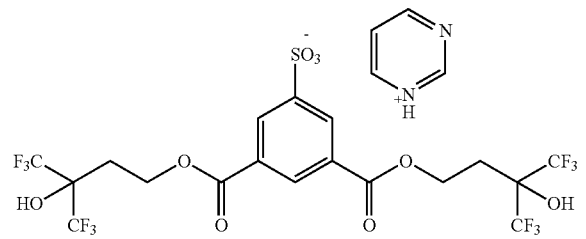
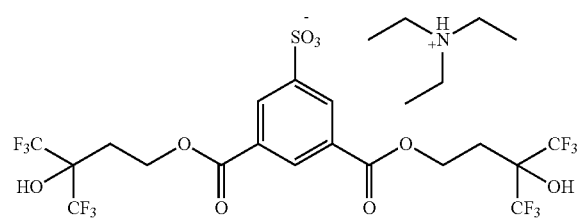
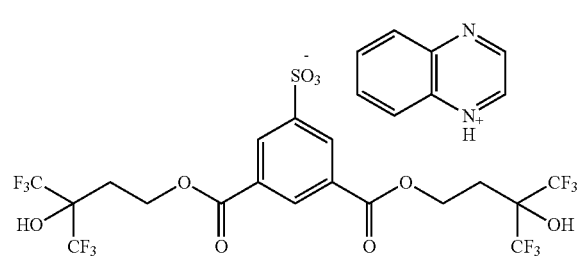
24
-continued
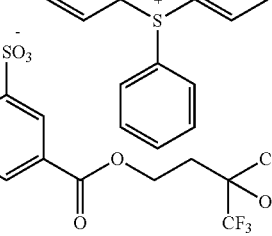
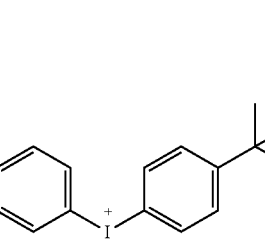
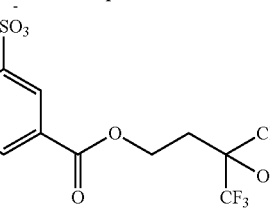
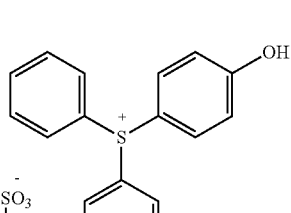
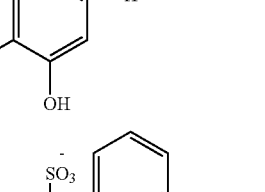
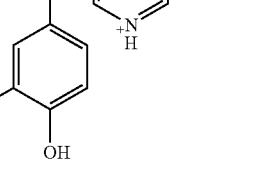

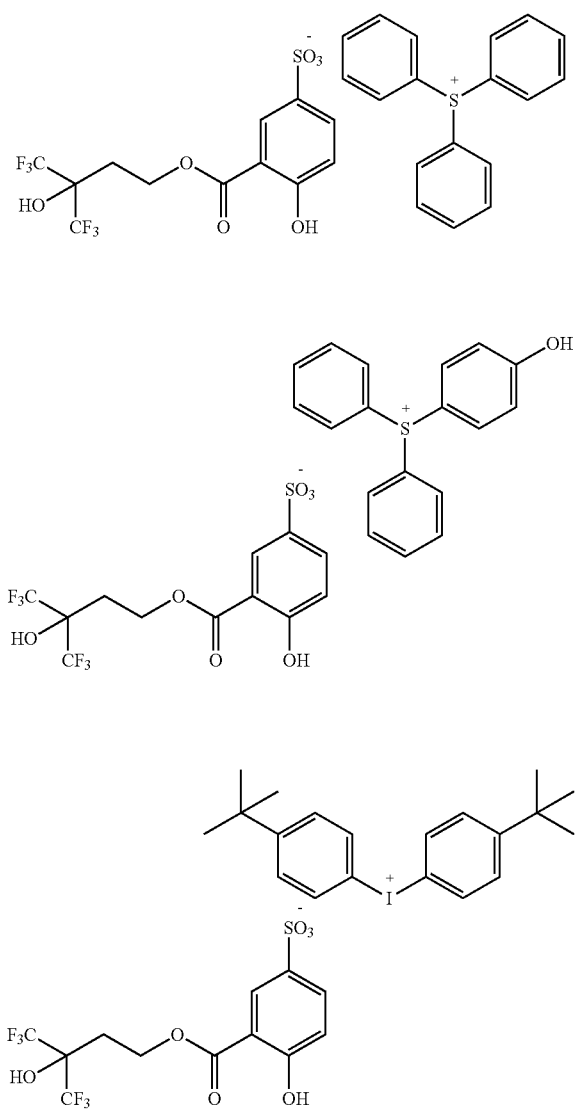

The TAGs typically have a weight average molecular weight Mw of from 300 to 2500, more typically from 500 to 1500. The thermal acid generator can typically be activated at a bake temperature of 100° C. or less, such as from 110 to 100° C., for example, from 80 to 90° C. or from 70 to 80° C. The thermal acid generator is typically present in the compositions in an amount of from 0.01 to 20 wt %, more typically from 0.1 to 10 wt % or from 1 to 5 wt %, based on total solids of the trimming composition.

Suitable thermal acid generators in accordance with the invention can be made by persons skilled in the art using known techniques and commercially available starting materials. For example, preferred thermal acid generators can be made by stirring a solution of free acid with an amine in a solvent, typically for a few hours. TAGs having a sulfonium or iodonium cation can be generated by mixing together a salt of the aromatic sulfonate anion with a salt of the sulfonium or iodonium cation in a solvent, typically for a few hours.

The trimming compositions further include a solvent or solvent mixture. Suitable solvent materials to formulate and cast the trimming compositions exhibit very good solubility characteristics with respect to the non-solvent components of the trimming composition, but do not appreciably dissolve the underlying photoresist pattern so as to minimize intermixing. The solvent is typically chosen from water, organic solvents and combinations thereof. Suitable organic solvents for the trimming composition include, for example: alkyl esters such as alkyl propionates such as n-butyl propionate, n-pentyl propionate, n-hexyl propionate and n-heptyl propionate, and alkyl butyrates such as n-butyl butyrate, isobutyl butyrate and isobutyl isobutyrate; ketones such as 2,5-dimethyl-4-hexanone and 2,6-dimethyl-4-heptanone; aliphatic hydrocarbons such as n-heptane, n-nonane, n-octane, n-decane, 2-methylheptane, 3-methylheptane, 3,3-dimethylhexane and 2,3,4-trimethylpentane, and fluorinated aliphatic hydrocarbons such as perfluoroheptane; alcohols such as straight, branched or cyclic $C_4$-$C_9$ monohydric alcohol such as 1-butanol, 2-butanol, isobutyl alcohol, tert-butyl alcohol, 3-methyl-1-butanol, 1-pentanol, 2-pentanol, 4-methyl-2-pentanol, 1-hexanol, 1-heptanol, 1-octanol, 2-hexanol, 2-heptanol, 2-octanol, 3-hexanol, 3-heptanol, 3-octanol and 4-octanol; 2,2,3,3,4,4-hexafluoro-1-butanol, 2,2,3,3,4,4,5,5-octafluoro-1-pentanol and 2,2,3,3,4,4,5,5,6,6-decafluoro-1-hexanol, and $C_5$-$C_9$ fluorinated diols such as 2,2,3,3,4,4-hexafluoro-1,5-pentanediol, 2,2,3,3,4,4,5,5-octafluoro-1,6-hexanediol and 2,2,3,3,4,4,5,5,6,6,7,7-dodecafluoro-1,8-octanediol; ethers such as isopentyl ether and dipropylene glycol monomethyl ether; and mixtures containing one or more of these solvents. Of these organic solvents, alcohols, aliphatic hydrocarbons and ethers are preferred. The solvent component of the trimming composition is typically present in an amount of from 90 to 99 wt %, more preferably from 95 to 99 wt %, based on the trimming composition.

The trimming compositions may include optional additives. For example, the trimming compositions can include an additional component that reacts with surface region of the resist pattern, rendering the surface region soluble in an organic solvent rinsing agent. This optional component preferably contains functional groups chosen from —OH, amine, —SH, ketones, aldehydes, —SiX wherein X is a halogen, vinyl ethers and combinations thereof. Without wishing to be bound by any particular theory, it is believed that the component diffuses into the resist pattern and reacts with carboxylic acid groups of the pattern. This reaction results in a polarity change of the surface, rendering the surface soluble in the organic solvent. This component can be useful, for example, where the photoresist pattern is formed by negative tone development (NTD) wherein the pattern is composed of exposed portions of the photoresist comprising acid-labile groups. Such component if used is typically present in an amount of from 0.1 to 10 wt % based on total solids of the trimming composition.

The trimming composition can further include a surfactant. Typical surfactants include those which exhibit an amphiphilic nature, meaning that they can be both hydrophilic and hydrophobic at the same time. Amphiphilic surfactants possess a hydrophilic head group or groups, which have a strong affinity for water and a long hydrophobic tail, which is organophilic and repels water. Suitable surfactants can be ionic (i.e., anionic, cationic) or nonionic. Further examples of surfactants include silicone surfactants, poly (alkylene oxide) surfactants, and fluorochemical surfactants. Suitable non-ionic surfactants include, but are not limited to, octyl and nonyl phenol ethoxylates such as TRITON® X-114, X-100, X-45, X-15 and branched secondary alcohol ethoxylates such as TERGITOL™ TMN-6 (The Dow Chemical Company, Midland, Mich. USA). Still further exemplary surfactants include alcohol (primary and secondary) ethoxylates, amine ethoxylates, glucosides, glucamine, polyethylene glycols, poly(ethylene glycol-co-propylene glycol), or other surfactants disclosed in *McCutcheon's Emulsifiers and Detergents*, North American Edition for the Year 2000 published by Manufacturers Confectioners Publishing Co. of Glen Rock, N.J. Nonionic surfactants that are acetylenic diol derivatives also can be suitable. Such surfactants are commercially available from Air Products and Chemicals, Inc. of Allentown, Pa. and sold under the trade names of SURFYNOL® and DYNOL®. Additional suitable surfactants include other polymeric compounds such as the tri-block EO-PO-EO co-polymers PLURONIC® 25R2, L121, L123, L31, L81, L101 and P123 (BASF, Inc.). Such surfactant and other optional additives if used are typically present in the composition in minor amounts such as from 0.01 to 10 wt % based on total solids of the trimming composition.

The trimming compositions are preferably free of crosslinking agents as such materials can result in a dimensional increase of the resist pattern.

The trimming compositions can be prepared following known procedures. For example, the compositions can be prepared by dissolving solid components of the composition in the solvent components. The desired total solids content of the compositions will depend on factors such as the desired final layer thickness. Preferably, the solids content of the trimming compositions is from 1 to 10 wt %, more preferably from 1 to 5 wt %, based on the total weight of the composition.

Photoresist Pattern Trimming Methods

Processes in accordance with the invention will now be described with reference to FIG. 1A-H, which illustrates an exemplary process flow for forming a photolithographic pattern using a photoresist pattern trimming technique in accordance with the invention. While the illustrated process flow is of a positive tone development process, the invention is also applicable to negative tone development (NTD) processes. Also, while the illustrated process flow describes a patterning process in which a single resist mask is used to transfer the trimmed photoresist pattern to the underlying substrate, it should be clear that the trimming method can be used in other lithographic processes, for example, in double patterning processes such as litho-litho-etch (LLE), litho-etch-litho-etch (LELE) or self-aligned double patterning (SADP), as an ion implantation mask, or any other lithographic process where trimming of a photoresist pattern would be beneficial.

FIG. 1A depicts in cross-section a substrate 100 which may include various layers and features. The substrate can be of a material such as a semiconductor, such as silicon or a compound semiconductor (e.g., III-V or II-VI), glass, quartz, ceramic, copper and the like. Typically, the substrate is a semiconductor wafer, such as single crystal silicon or compound semiconductor wafer, and may have one or more layer and patterned features formed on a surface thereof. One or more layer to be patterned 102 may be provided over the substrate 100. Optionally, the underlying base substrate material itself may be patterned, for example, when it is desired to form trenches in the substrate material. In the case of patterning the base substrate material itself, the pattern shall be considered to be formed in a layer of the substrate.

The layers may include, for example, one or more conductive layer such as layers of aluminum, copper, molybdenum, tantalum, titanium, tungsten, alloys, nitrides or silicides of such metals, doped amorphous silicon or doped polysilicon, one or more dielectric layer such as layers of silicon oxide, silicon nitride, silicon oxynitride, or metal oxides, semiconductor layers, such as single-crystal silicon, and combinations thereof. The layers to be etched can be formed by various techniques, for example, chemical vapor deposition (CVD) such as plasma-enhanced CVD, low-pressure CVD or epitaxial growth, physical vapor deposition (PVD) such as sputtering or evaporation, or electroplating. The particular thickness of the one or more layer to be etched 102 will vary depending on the materials and particular devices being formed.

Depending on the particular layers to be etched, film thicknesses and photolithographic materials and process to be used, it may be desired to dispose over the layers 102 a hard mask layer 103 and/or a bottom antireflective coating (BARC) 104 over which a photoresist layer 106 is to be coated. Use of a hard mask layer may be desired, for example, with very thin resist layers, where the layers to be etched require a significant etching depth, and/or where the particular etchant has poor resist selectivity. Where a hard mask layer is used, the resist patterns to be formed can be transferred to the hard mask layer 103 which, in turn, can be used as a mask for etching the underlying layers 102. Suitable hard mask materials and formation methods are known in the art. Typical materials include, for example, tungsten, titanium, titanium nitride, titanium oxide, zirconium oxide, aluminum oxide, aluminum oxynitride, hafnium oxide, amorphous carbon, silicon oxynitride and silicon nitride. The hard mask layer can include a single layer or a plurality of layers of different materials. The hard mask layer can be formed, for example, by chemical or physical vapor deposition techniques.

A bottom antireflective coating may be desirable where the substrate and/or underlying layers would otherwise reflect a significant amount of incident radiation during photoresist exposure such that the quality of the formed pattern would be adversely affected. Such coatings can improve depth-of-focus, exposure latitude, linewidth uniformity and CD control. Antireflective coatings are typically used where the resist is exposed to deep ultraviolet light (300 nm or less), for example, KrF excimer laser light (248 nm) or ArF excimer laser light (193 nm). The antireflective coating can comprise a single layer or a plurality of different layers. Suitable antireflective materials and methods of formation are known in the art. Antireflective materials are commercially available, for example, those sold under the AR™ trademark by Rohm and Haas Electronic Materials LLC (Marlborough, Mass. USA), such as AR™40A and AR™124 antireflectant materials.

A photoresist layer 106 is formed from a photoresist material, typically a chemically amplified photosensitive composition, comprising a matrix polymer having acid labile groups. The photoresist layer is disposed on the substrate over the antireflective layer 104 (if present). The photoresist composition can be applied to the substrate by spin-coating, dipping, roller-coating or other conventional coating technique. Of these, spin-coating is typical. For spin-coating, the solids content of the coating solution can be adjusted to provide a desired film thickness based upon the specific coating equipment utilized, the viscosity of the solution, the speed of the coating tool and the amount of time allowed for spinning. A typical thickness for the photoresist layer 106 is from about 500 to 3000 Å.

The photoresist layer 106 can next be softbaked to minimize the solvent content in the layer, thereby forming a tack-free coating and improving adhesion of the layer to the substrate. The softbake can be conducted on a hotplate or in an oven, with a hotplate being typical. The softbake temperature and time will depend, for example, on the particular material of the photoresist and thickness. Typical softbakes are conducted at a temperature of from about 90 to 150° C., and a time of from about 30 to 90 seconds.

The photoresist layer 106 is next exposed to activating radiation 108 through a photomask 110 to create a difference in solubility between exposed and unexposed regions. References herein to exposing a photoresist composition to radiation that is activating for the composition indicates that the radiation is capable of forming a latent image in the photoresist composition. The photomask has optically transparent and optically opaque regions corresponding to regions of the resist layer to be exposed and unexposed, respectively, by the activating radiation. The exposure wavelength is typically sub-400 nm, sub-300 nm or sub-200 nm such as 193 nm or an EUV wavelengths (e.g., 13.4 or 13.5 nm), with 193 nm (immersion or dry lithography) and EUV being preferred. The exposure energy is typically from about 10 to 80 mJ/cm$^2$, dependent upon the exposure tool and the components of the photosensitive composition.

Following exposure of the photoresist layer 106, a post-exposure bake (PEB) is typically performed. The PEB can be conducted, for example, on a hotplate or in an oven. Conditions for the PEB will depend, for example, on the particular photoresist composition and layer thickness. The PEB is typically conducted at a temperature of from about 80 to 150° C., and a time of from about 30 to 90 seconds. A latent image defined by the boundary between polarity-switched and unswitched regions (corresponding to exposed and unexposed regions, respectively) is thereby formed.

Figure 1E:
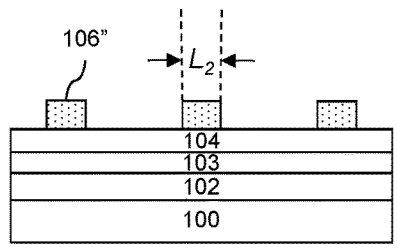
Figure 1B:
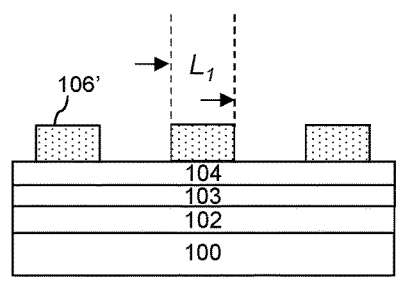

The photoresist layer 106 is next developed to remove exposed regions of the layer, leaving unexposed regions forming a resist pattern 106' having a plurality of features as shown in FIG. 1B. The features are not limited and can include, for example, a plurality of lines and/or cylindrical posts which will allow for the formation of line and/or contact hole patterns in the underlying layers to be patterned. The formed patterns have an initial dimension shown as $L_1$, a linewidth in the case of line patterns or post diameter for post patterns. In the case of a negative tone development process, where unexposed regions of the photoresist layer are removed and exposed regions remain to form the resist pattern, an organic solvent developer is typically employed. The organic solvent developer can, for example, be a solvent chosen from ketones, esters, ethers, hydrocarbons, and mixtures thereof, with 2-heptanone and n-butyl acetate being typical.

Figure 1F:
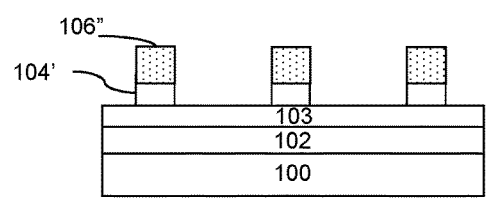
Figure 1C:
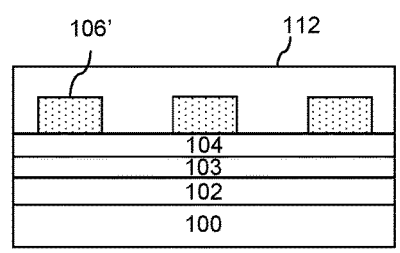

A layer 112 of a photoresist pattern trimming composition as described herein is formed over the photoresist pattern 106' as shown in FIG. 1C. The trimming composition is typically applied to the substrate by spin-coating. The solids content of the coating solution can be adjusted to provide a desired film thickness based upon the specific coating equipment utilized, the viscosity of the solution, the speed of the coating tool and the amount of time allowed for spinning. A typical thickness for the pattern trimming layer 112 is from 200 to 1500 Å, typically measured on an unpatterned substrate.

Figure 1G:
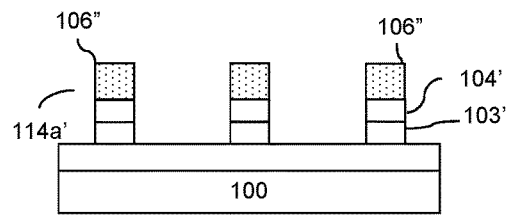
Figure 1D:
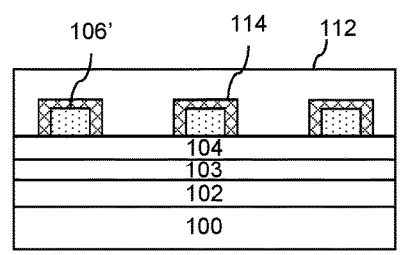

As shown in FIG. 1D, the substrate is next baked to remove solvent in the trimming composition layer, activate the thermal acid generator and allow the generated acid to diffuse into the surface of the resist pattern 106' to cause the polarity-changing reaction in the resist pattern surface region 114. The bake can be conducted with a hotplate or oven, with a hotplate being typical. Suitable bake temperatures are greater than 50° C., for example, greater than 70° C., greater than 90° C., greater than 120° C. or greater than 150° C., with a temperature of from 70 to 160° C. and a time of from about 30 to 90 seconds being typical. While a single baking step is typical, multiple-step baking can be used and may be useful for resist profile adjustment.

The photoresist pattern is next contacted with a rinsing agent, typically a developing solution, to remove the residual trimming composition layer 112 and the surface region 114 of the photoresist pattern, with the resulting trimmed pattern 106" being shown in FIG. 1E. The rinsing agent is typically an aqueous alkaline developer, for example, a quaternary ammonium hydroxide solution, for example, a tetra-alkyl ammonium hydroxide solutions such as 0.26 Normality (N) (2.38 wt %) tetramethylammonium hydroxide (TMAH). Alternatively, an organic solvent developer can be used, for example, a solvent chosen from ketones, esters, ethers, hydrocarbons, and mixtures thereof, such as 2-heptanone and n-butyl acetate. The rinsing agent can further be or comprise water. The resulting structure is shown in FIG. 1E. The resist pattern after trimming has a dimension ($L_2$) that is smaller as compared with the feature size prior to trimming.

Figure 1H:
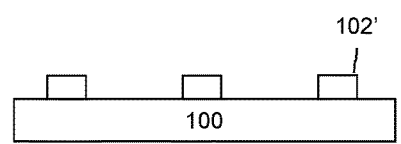

Using the resist pattern 106″ as an etch mask, the BARC layer 104 is selectively etched to form BARC patterns 104′, exposing the underlying hardmask layer 103, as shown in FIG. 1F. The hardmask layer is next selectively etched, again using the resist pattern as an etch mask, resulting in patterned BARC and hardmask layer 103′, as shown in FIG. 1G. Suitable etching techniques and chemistries for etching the BARC layer and hardmask layer are known in the art and will depend, for example, on the particular materials of these layers. Dry-etching processes such as reactive ion etching are typical. The resist pattern 106″ and patterned BARC layer 104′ are next removed from the substrate using known techniques, for example, oxygen plasma ashing. Using the hardmask pattern 103′ as an etch mask, the one or more layer 102 are then selectively etched. Suitable etching techniques and chemistries for etching the underlying layers 102 are known in the art, with dry-etching processes such as reactive ion etching being typical. The patterned hardmask layer 103′ can next be removed from the substrate surface using known techniques, for example, a dry-etching process such as reactive ion etching or a wet strip. The resulting structure is a pattern of etched features 102′ as illustrated in FIG. 1H. In an alternative exemplary method, it may be desirable to pattern the layer 102 directly using the photoresist pattern 106″ without the use of a hardmask layer 103. Whether direct patterning with the resist patterns can be employed will depend on factors such as the materials involved, resist selectivity, resist pattern thickness and pattern dimensions.

The following non-limiting examples are illustrative of the invention.

EXAMPLES

The thermal acid generators shown in Table 1 were used in the examples described below.

TABLE 1

| TAG No. | TAG Name | Structure | Anion MW | Anion Molar Vol (cm$^3$) |
|---|---|---|---|---|
| TAG-1 (Comp.) | 3FP PFBuS | 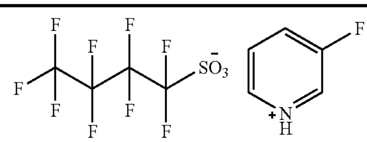 | 299.09 | 159.74 |
| TAG-2 (Comp.) | Pyrimidinium PFBuS | 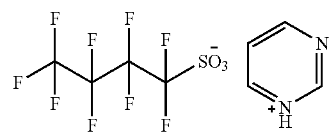 | 299.09 | 159.74 |
| TAG-3 | 3FP SIPA DiHFA | 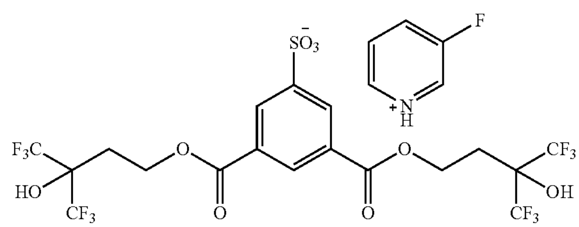 | 633.33 | 418.13 |
| TAG-4 | Pyr SIPA DiHFA | 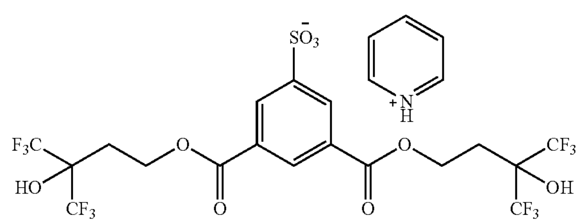 | 633.33 | 418.13 |
| TAG-5 | Pyrimidinium SIPA DiHFA | 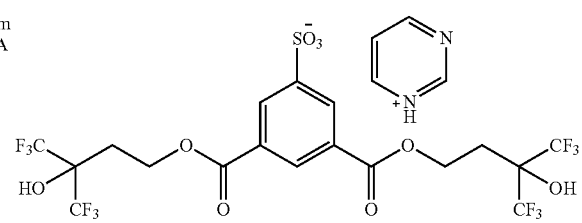 | 633.33 | 418.13 |

Thermal Acid Generator Synthesis

Example 1: Synthesis of TAG-3

3-Fluoropyridin-1-ium3,5-bis((4,4,4-trifluoro-3-hydroxy-3-(trifluoromethyl) butoxy)carbonyl)benzenesulfonate (3FP SIPA-DiHFA) (TAG-3) was prepared according to the reaction sequence shown below in Scheme 1.

Scheme 1: Synthesis of TAG-3 (3FP SIPA-DiHFA)

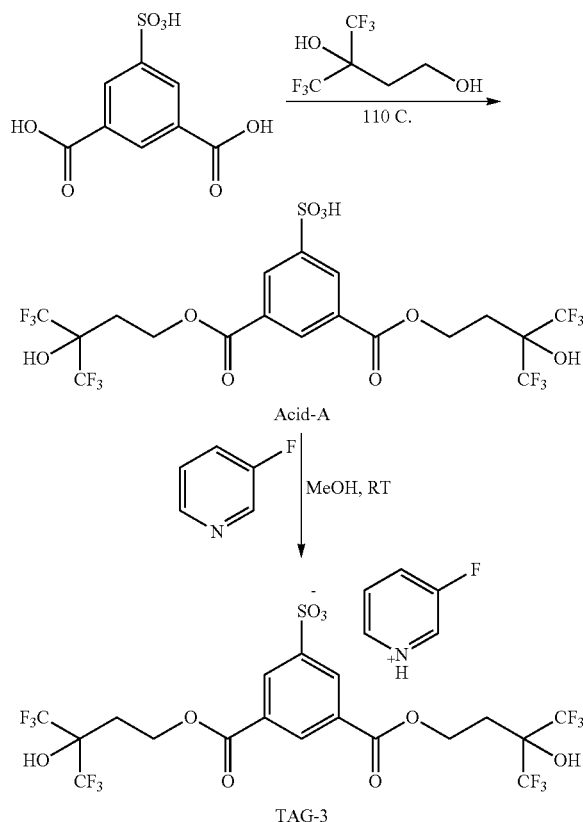

Synthesis of 3,5-bis((4,4,4-trifluoro-3-hydroxy-3-(trifluoromethyl)butoxy)carbonyl) benzene sulfonic acid (Acid-A)

5-Sulfoisophthalic acid (6.3 g, 24.3 mmol) as a 50 wt % water solution was mixed with 15 g (70.7 mmol) of 4,4,4-trifluoro-3-(trifluoromethyl)butane-1,3-diol at room temperature, under nitrogen flow. The temperature of the reaction mixture was then raised to 110-120° C. At this temperature, the reaction was carried out for 2-3 hours with constant evaporation of water as a side product. The reaction mixture was then poured into a 1M HCl aqueous solution. After 5-10 minutes, the mixture separated into two layers. The organic layer was recovered, washed three times with 1M HCl aqueous solution, and then extracted with diethyl ether. The crude product was then dried over MgSO$_4$. The volatile contaminants were removed by rotary evaporation. The crude product was further washed with heptanes:acetone (8:2) to yield solid acid A in 64% yield. $^1$H NMR ((CD$_3$)$_2$CO, 500 MHz): δ 2.63 (t, 4H), 4.68 (t, 4H), 7.11 (bs, 3H), 8.68 (m, 3H). 19F NMR ((CD$_3$)$_2$CO, 500 MHz): δ–76.56.

Synthesis of 3-fluoropyridin-1-ium3,5-bis((4,4,4-trifluoro-3-hydroxy-3-(trifluoromethyl) butoxy)carbonyl)benzenesulfonate (3FP SIPA-DiHFA) TAG-3

To the solution of 3,5-bis((4,4,4-trifluoro-3-hydroxy-3-(trifluoromethyl)butoxy)carbonyl)benzenesulfonic acid (Acid-A) (32 g, 48.33 mmol) in methanol (200 mL) was added 3-fluoropyridine (7 g, 72.14 mmol). The resulting mixture was stirred at room temp overnight. Upon completion, the reaction mixture was concentrated under reduced pressure. Heptane (300 mL) was added to the resulting crude product as gue and let the mixture stand over 2 h. Slowly gue started to form into solids. White solids were filtered and washed with heptanes and dichloromethane to yield pure product 3-Fluoropyridin-1-ium3,5-bis((4,4,4-trifluoro-3-hydroxy-3-(trifluoromethyl)butoxy) carbonyl) benzenesulfonate (3FP SIPA-DiHFA) (TAG-3) in 90% yield (32 g). $^1$H NMR (CDCl$_3$, 500 MHz): δ 2.17 (t, 4H), 4.14 (t, 4H), 7.30 (m, 4H), 8.45 (m, 3H). $^{19}$F NMR ((CD$_3$)$_2$CO, 500 MHz): δ–76.56, –123.06.

Example 2: Synthesis of TAG-4

Pyridin-1-ium 3,5-bis((4,4,4-trifluoro-3-hydroxy-3-(trifluoromethyl)butoxy) carbonyl)benzenesulfonate (Pyr SIPA-DiHFA) (TAG-4) was prepared according to the reaction sequence shown below in Scheme 2.

Scheme 2: Synthesis of TAG-4 (Pyr SIPA-DiHFA)

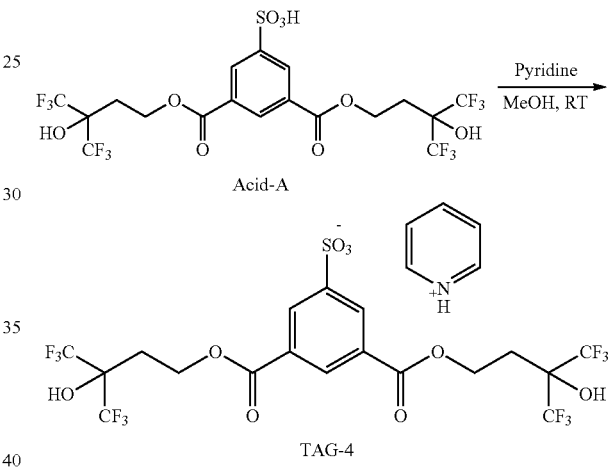

Synthesis of pyridin-1-ium 3,5-bis((4,4,4-trifluoro-3-hydroxy-3-(trifluoromethyl)butoxy) carbonyl)benzenesulfonate (Pyr SIPA-DiHFA) TAG-4: The compound TAG-4 was synthesized following same procedure as shown above in example TAG-3 in 90% yield as white solids. $^1$H NMR ((CD$_3$)$_2$CO, 500 MHz): δ 2.63 (t, 4H), 4.68 (t, 4H), 7.11 (bs, 3H), 8.68 (m, 3H), 8.50 (m, 2H), 9.16 (m, 1H), 9.23 (m, 2H). $^{19}$F NMR ((CD$_3$)$_2$CO, 500 MHz): δ–76.62

Example 3: Synthesis of TAG-5

Pyrimidin-1-ium 3,5-bis((4,4,4-trifluoro-3-hydroxy-3-(trifluoromethyl)butoxy) carbonyl)benzenesulfonate (Pyrimidinium SIPA-DiHFA) (TAG-5) was prepared according to the reaction sequence shown below in Scheme 3.

Scheme 3: Synthesis of TAG-5 (Pyrimidinium SIPA-DiHFA)

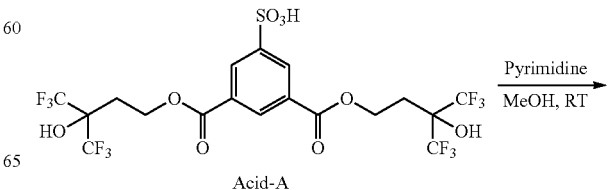

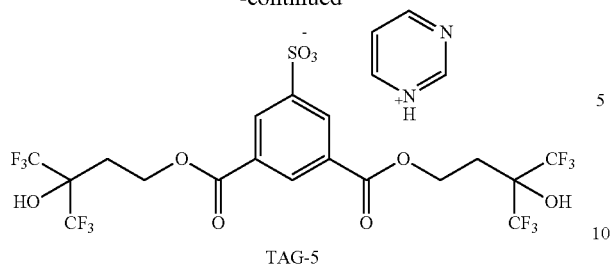

TAG-5

Synthesis of pyrimidin-1-ium 3,5-bis((4,4,4-trifluoro-3-hydroxy-3-(trifluoromethyl)butoxy) carbonyl)benzenesulfonate (Pyrimidinium SIPA-DiHFA) TAG-5: The compound TAG-5 was synthesized following same procedure as shown in example TAG-3 in 86% yield as white solids. $^1$H NMR (DMSO-d$^6$, 500 MHz): δ 2.59 (t, 4H), 4.63 (t, 4H), 7.65 (bs, 1H), 8.51 (m, 3H), 8.92 (BS, 2H), 9.30 (bs, 1H). $^{19}$F NMR ((CD$_3$)$_2$CO, 500 MHz): δ −76.48.

Photoresist Composition Preparation

The following monomers M1-M5 were used to form polymers for preparation of the photoresist (Photoresist Composition A) described below:

M1
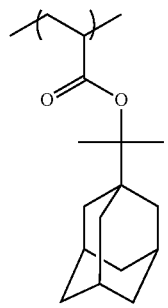

M2
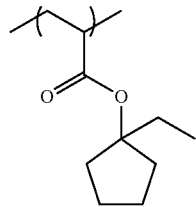

M3
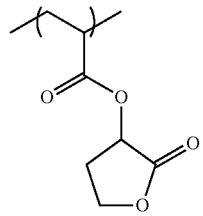

M4
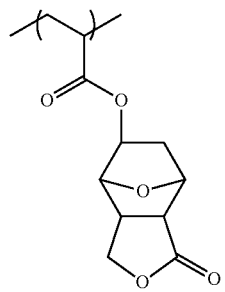

M5
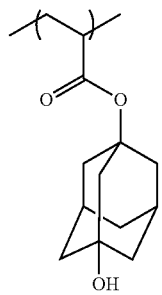

A positive chemically amplified photoresist composition was prepared by combining 4.54 g Polymer A (M1/M2/M3/M4/M5=2/1/4/1/2 mole ratio, MW=10K), 0.401 g of (4-t-butylphenyl)tetramethylene sulfonium norbornyl perfluoroethoxyethylsulfonate (TBPTMS-NBPFEES), 0.178 g triphenylsulfonium 4,4,5,5,6,6-hexafluorodihydro-4H-1,3,2-dithiazine 1,1,3,3-tetraoxide (TPS-PFSI-CY6), 0.039 g of 1-(tertbutyoxycarbonyl)-4-hydroxypiperidine (TBOC-4HP), 0.008 g of POLYFOX 656 surfactant (Omnova Solutions Inc.), 75.87 g propylene glycol methyl ether acetate and 18.97 g cyclohexanone.

Photoresist Patterned Wafer Preparation 8-inch silicon wafers coated with an 80 nm BARC layer (AR™40A antireflectant, Dow Electronic Materials, Marlborough, Mass. USA) were spin-coated with Photoresist Composition A and softbaked at 100° C. for 60 seconds to provide a resist layer thickness of 900 Å. The wafers were exposed using an ASML ArF 1100 scanner with NA=0.75, Dipole 35Y illumination (0.89/0.64sigma), using a mask having line and space patterns with PSM feature size of 120 nm 1:1 and 1:8, under dipole-35Y with outer/inner sigma of 0.89/0.64. The exposed wafers were post-exposure baked at 100° C. for 60 seconds and developed with a 0.26N TMAH solution to form a 120 nm 1:1 and 1:8 line and space pattern (duty ratio=1:1) imaged resist layer. CDs for the patterns were determined by processing the image captured by top-down scanning electron microscopy (SEM) using a Hitachi 9380 CD-SEM, operating at an accelerating voltage of 500 volts (V), probe current of 5.0 picoamperes (pA), using 150 Kx magnification. Three exposure latitudes were taken for each wafer and averaged. The average exposure latitude was then fit using a polynomial regression to determine the correct sizing dose of the 120 nm lines for the case of no resist pattern trimming. This sizing dose was then used with the polynomial regression of the resist pattern-trimmed wafers to calculate the final CD of each pattern-trimmed wafer. The results of the CD measurements are shown in Table 2.

Photoresist Trimming Compositions, Pattern Trimming and Evaluation

Example 4: Comparative (PTC-1)

0.202 g copolymer of n-butylmethacrylate/methacrylic acid polymer (77/23 weight ratio), 0.014 g 3-fluoropyridin-1-ium 1,1,2,2,3,3,4,4,4-nonafluorobutane-1-sulfonate TAG 1 (3FP PFBuS), 7.827 g methyl isobutyl carbinol and 1.957 g isoamyl ether were mixed until all components dissolved. The mixture was filtered with a 0.2 micron Nylon filter, resulting in photoresist trimming composition PTC-1. A 60 nm film of PTC-1 was spin-coated on photoresist-patterned wafers as prepared above, baked at 70° C. or 90° C. for 60 seconds on a hotplate and developed in 2.38 wt % TMAH developer for 12 seconds with an SH nozzle. CDs of the trimmed patterns were measured in the same manner as the pre-trimmed patterns, with the results shown in Table 2.

Example 5: Comparative (PTC-2)

0.203 g copolymer of n-butylmethacrylate/methacrylic acid polymer (77/23 weight ratio), 0.013 g pyrimidin-1-ium 1,1,2,2,3,3,4,4,4-nonafluorobutane-1-sulfonate TAG 2 (Pyrimidinium PFBuS), 7.827 g methyl isobutyl carbinol and 1.957 g isoamyl ether were mixed until all components dissolved. The content of TAG-2 in PTC-2 is equimolar to the TAG 1 content in Example 1. The mixture was filtered with a 0.2 micron Nylon filter, resulting in photoresist trimming composition PTC-2. A 60 nm film of PTC-2 was spin-coated on photoresist-patterned wafers as prepared above, baked at temperatures of 70° C. or 90° C. for 60 seconds on a hotplate, and developed in 2.38 wt % TMAH developer for 12 seconds with an SH nozzle. CDs of the trimmed patterns were measured in the same manner as the pre-trimmed patterns, with the results shown in Table 2.

Example 6: (PTC-3)

0.191 g copolymer of n-butylmethacrylate/methacrylic acid polymer (77/23 weight ratio), 0.025 g 3-fluoropyridin-1-ium3,5-bis((4,4,4-trifluoro-3-hydroxy-3-(trifluoromethyl)butoxy)carbonyl)benzenesulfonate TAG-3 (3FP SIPA-DiHFA), 7.827 g methyl isobutyl carbinol and 1.957 g isoamyl ether were mixed until all components dissolved. The content of TAG-3 in PTC-3 is equimolar to the TAG-1 content in Example 1. The mixture was filtered with a 0.2 micron Nylon filter, resulting in photoresist trimming composition PTC-3. A 60 nm film of PTC-3 was spin-coated on a photoresist-patterned wafer as prepared above, baked at a temperature of 90° C. for 60 seconds on a hotplate, and developed in 2.38 wt % TMAH developer for 12 seconds with an SH nozzle. CDs of the trimmed patterns were measured in the same manner as the pre-trimmed patterns, with the results shown in Table 2.

Example 7: (PTC-4)

0.191 g copolymer of n-butylmethacrylate/methacrylic acid polymer (77/23 weight ratio), 0.025 g pyridin-1-ium 3,5-bis((4,4,4-trifluoro-3-hydroxy-3-(trifluoromethyl)butoxy)carbonyl) benzenesulfonate TAG-4 (Pyr SIPA-DiHFA), 7.827 g methyl isobutyl carbinol and 1.957 g isoamyl ether were mixed until all components dissolved. The content of TAG-4 in PTC-4 is equimolar to the TAG-1 content in Example 1. The mixture was filtered with a 0.2 micron Nylon filter, resulting in photoresist trimming composition PTC-4. A 60 nm film of PTC-4 was spin-coated on photoresist-patterned wafers as prepared above, baked at a temperature of 90° C. or 105° C. for 60 seconds on a hotplate, and developed in 2.38 wt % TMAH developer for 12 seconds with an SH nozzle. CDs of the trimmed patterns were measured in the same manner as the pre-trimmed patterns, with the results shown in Table 2.

Example 8: (PTC-5)

0.191 g copolymer of n-butylmethacrylate/methacrylic acid polymer (77/23 weight ratio), 0.025 g pyrimidin-1-ium 3,5-bis((4,4,4-trifluoro-3-hydroxy-3-(trifluoromethyl)butoxy) carbonyl) benzenesulfonate TAG-5 (Pyrimidinium SIPA-DiHFA), 7.827 g methyl isobutyl carbinol and 1.957 g isoamyl ether were mixed until all components dissolved. The content of TAG-5 in PTC-5 is equimolar to the TAG-1 content in Example 1. The mixture was filtered with a 0.2 micron Nylon filter, resulting in photoresist trimming composition PTC-5. A 60 nm film of PTC-5 was spin-coated on photoresist-patterned wafers as prepared above, baked at a temperature of 90° C. or 105° C. for 60 seconds on a hotplate, and developed in 2.38 wt % TMAH developer for 12 seconds with an SH nozzle. CDs of the trimmed patterns were measured in the same manner as the pre-trimmed patterns, with the results shown in Table 2.

Iso-Dense Bias

Iso-dense bias was calculated for various samples using the following equation:

$$IDB = \Delta CD_{1:8} - \Delta CD_{1:1}$$

wherein: IDB=iso-dense bias; $\Delta CD_{1:8}$=[(CD of the 120 nm 1:8 pattern before trimming)−(CD of the 120 nm 1:8 pattern after trimming)]; and $\Delta CD_{1:1}$=[(CD of the 120 nm 1:1 pattern before trimming)−(CD of the 120 nm 1:1 pattern after trimming)]. An iso-dense bias of 10 nm or more was considered poor and less than 10 nm good, with lower values indicating improved iso-dense bias relative to higher values. The results are provided in Table 2.

TABLE 2

| Example | Trim Composition | TAG | Bake Temp/Time (° C./sec) | Final CD (nm) | ΔCD (nm) | Iso-Dense Bias (nm) |
|---|---|---|---|---|---|---|
| before trim | — | — | — | 119.94 | 0 | — |
| 4 (Comp) | PTC-1 | 3FP PFBuS | 70 | 100.54 | 19.4 | 5.75 |
|  |  |  | 90 | 74.38 | 45.56 | — |
| 5 (Comp) | PTC-2 | Pyrimidinium PFBuS | 70 | 100.2 | 19.74 | 6.56 |
|  |  |  | 90 | 74.32 | 45.62 | — |
| 6 | PTC-3 | 3FP SIPA-DiHFA | 90 | 106.31 | 13.63 | 2.2 |
| 7 | PTC-4 | Pyr SIPA-DiHFA | 90 | 109.44 | 10.5 | — |
|  |  |  | 105 | 105.19 | 14.75 | 2.9 |
| 8 | PTC-5 | Pyrimidinium SIPA-DiHFA | 90 | 115 | 4.94 | — |
|  |  |  | 105 | 114.15 | 5.79 | — |

As can be seen from Table 2, trimming compositions PTC-3 to PTC-5 containing bulky aromatic sulfonate TAG anions resulted in resist patterns having lower trim amounts at the same or higher temperature than that of comparative compositions PTC-1 and PTC-2 containing a smaller non-aromatic sulfonate TAG anion. The lower trim values are believed to be a result of the relatively bulky anions of the PTC-3 to PTC-5 TAGs as compared with that of the TAGs of the comparative examples. Iso-dense bias was improved (lower) for trimming compositions PTC-3 and PTC-4 than for comparative compositions PTC-1 and PTC-2. Each of the trimming compositions tested at different bake temperatures exhibited an increased trim amount with increasing temperature, indicative of increased diffusion of the acid into the resist with associated deprotection reaction.

What is claimed is:

1. An ionic thermal acid generator, comprising: an anion of an aromatic sulfonic acid comprising one or more fluorinated alcohol group, wherein the anion comprises a fluoroalcohol group of the formula —C(CF$_3$)$_2$OH; and a cation.

2. The ionic thermal acid generator of claim 1, wherein the anion comprises a plurality of fluorinated alcohol groups of the formula —C(CF$_3$)$_2$OH.

3. The ionic thermal acid generator of claim 1, wherein the fluorinated alcohol group is bonded to an aromatic ring of the anion through an ester group.

4. The ionic thermal acid generator of claim 1, wherein the thermal acid generator is of the following general formula (I):

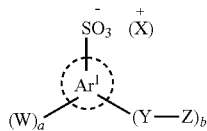

wherein: Ar$^1$ represents an optionally substituted carbocyclic or heterocyclic aromatic group; W independently represents a group chosen from carboxyl, hydroxy, nitro, cyano, C1-5 alkoxy and formyl; X is a cation; Y independently represents a linking group; Z independently represents a group chosen from hydroxyl, fluorinated alcohols, esters, optionally substituted alkyl, C5 or higher optionally substituted monocyclic, polycyclic, fused polycyclic cycloaliphatic, or aryl, which may optionally comprise a heteroatom, provided at least one occurrence of Z is a fluorinated alcohol group; a is an integer of 0 or greater; b is an integer of 1 or greater; provided that a+b is at least 1 and not greater than the total number of available aromatic carbon atoms of the aromatic group.

5. An ionic thermal acid generator, comprising: an anion of an aromatic sulfonic acid comprising one or more fluorinated alcohol group, and a cation, wherein the fluorinated alcohol group comprises: a fluorine atom bonded to a carbon at the alpha position of the hydroxyl group and/or a fluorinated group bonded pendant to a carbon at the alpha position of the hydroxyl group.

6. The ionic thermal acid generator of claim 5, wherein the thermal acid generator anion is chosen from the following:

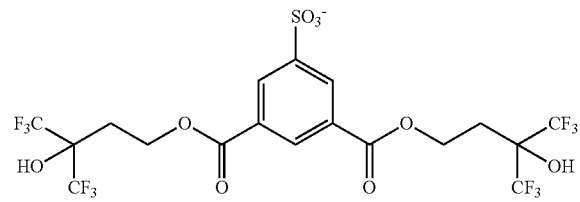

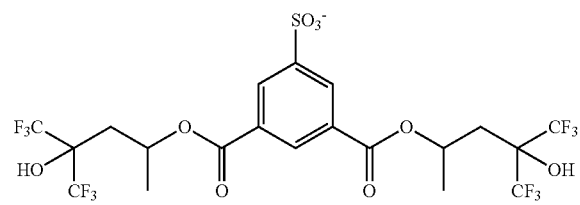

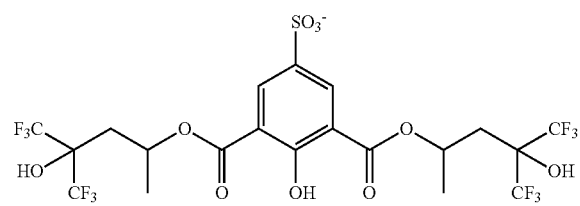

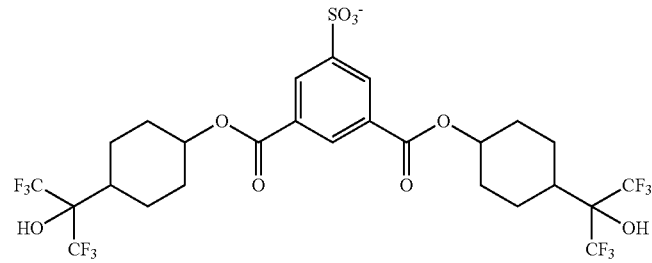

-continued
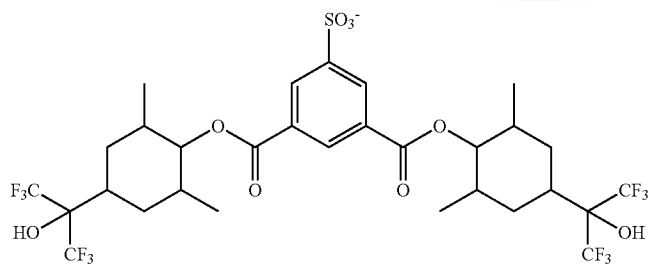
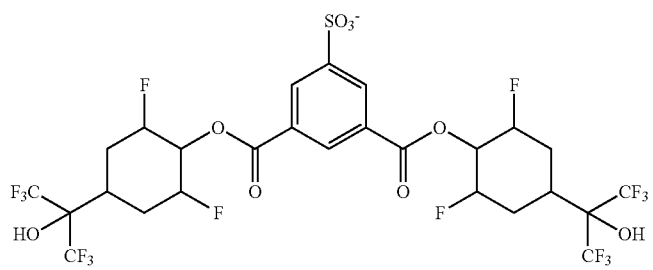
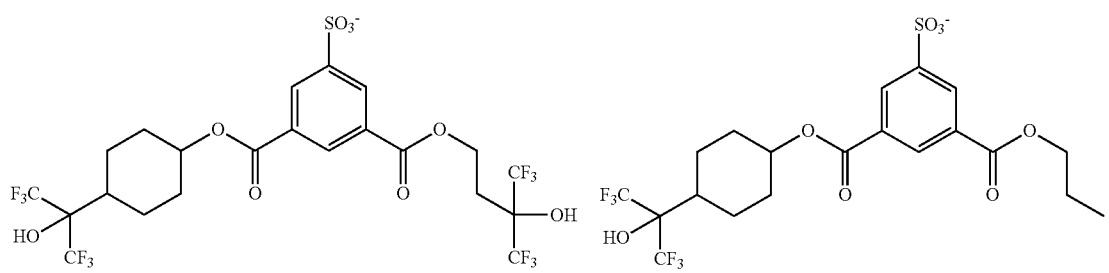
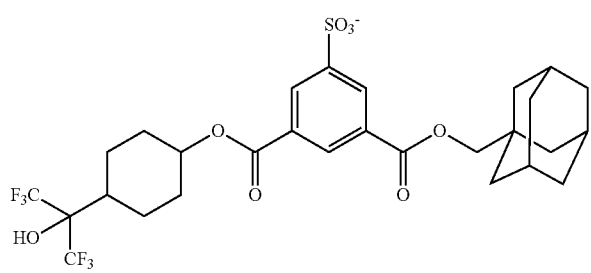
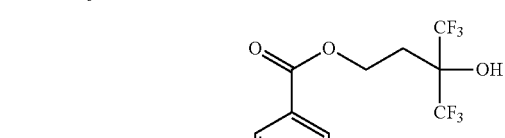
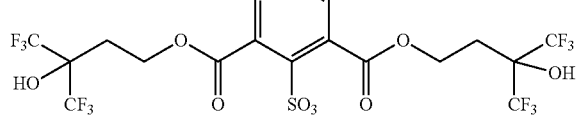
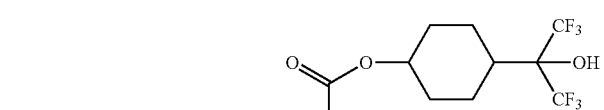
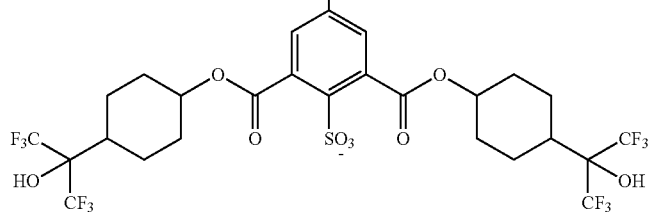

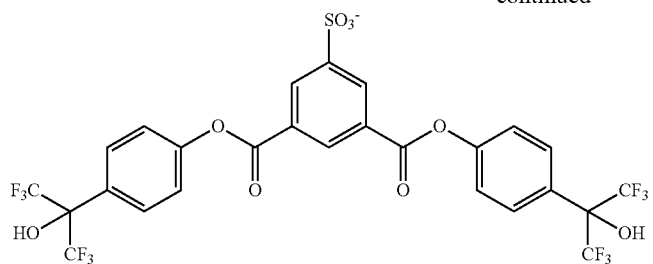
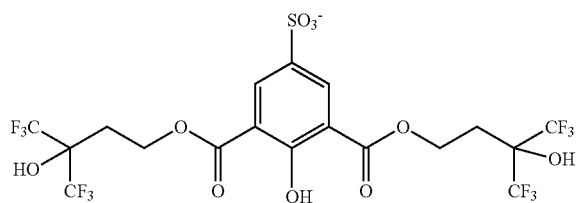
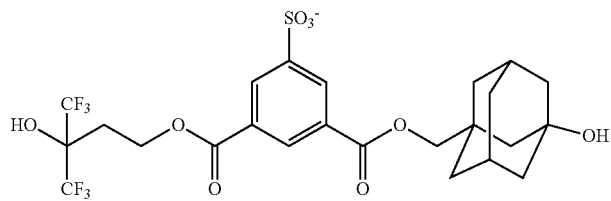
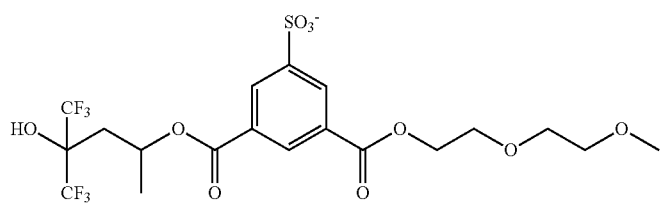
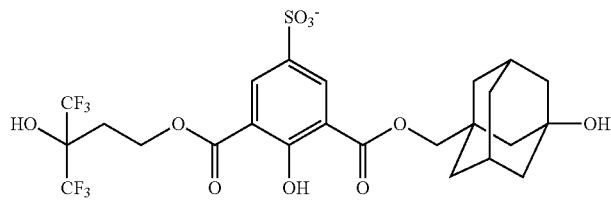
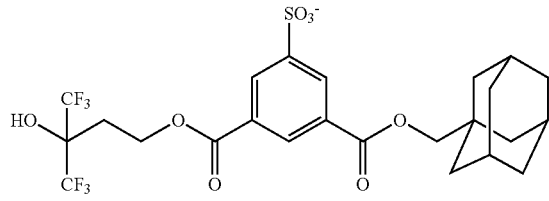
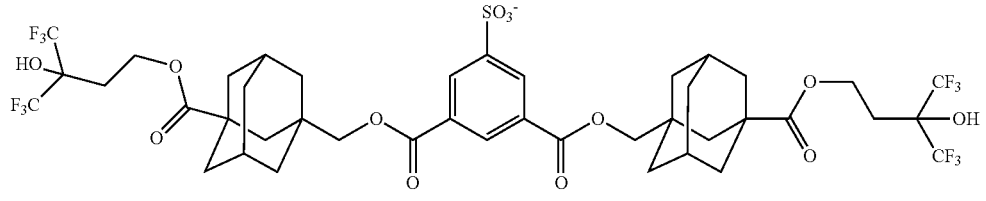
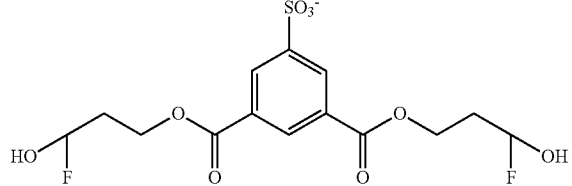

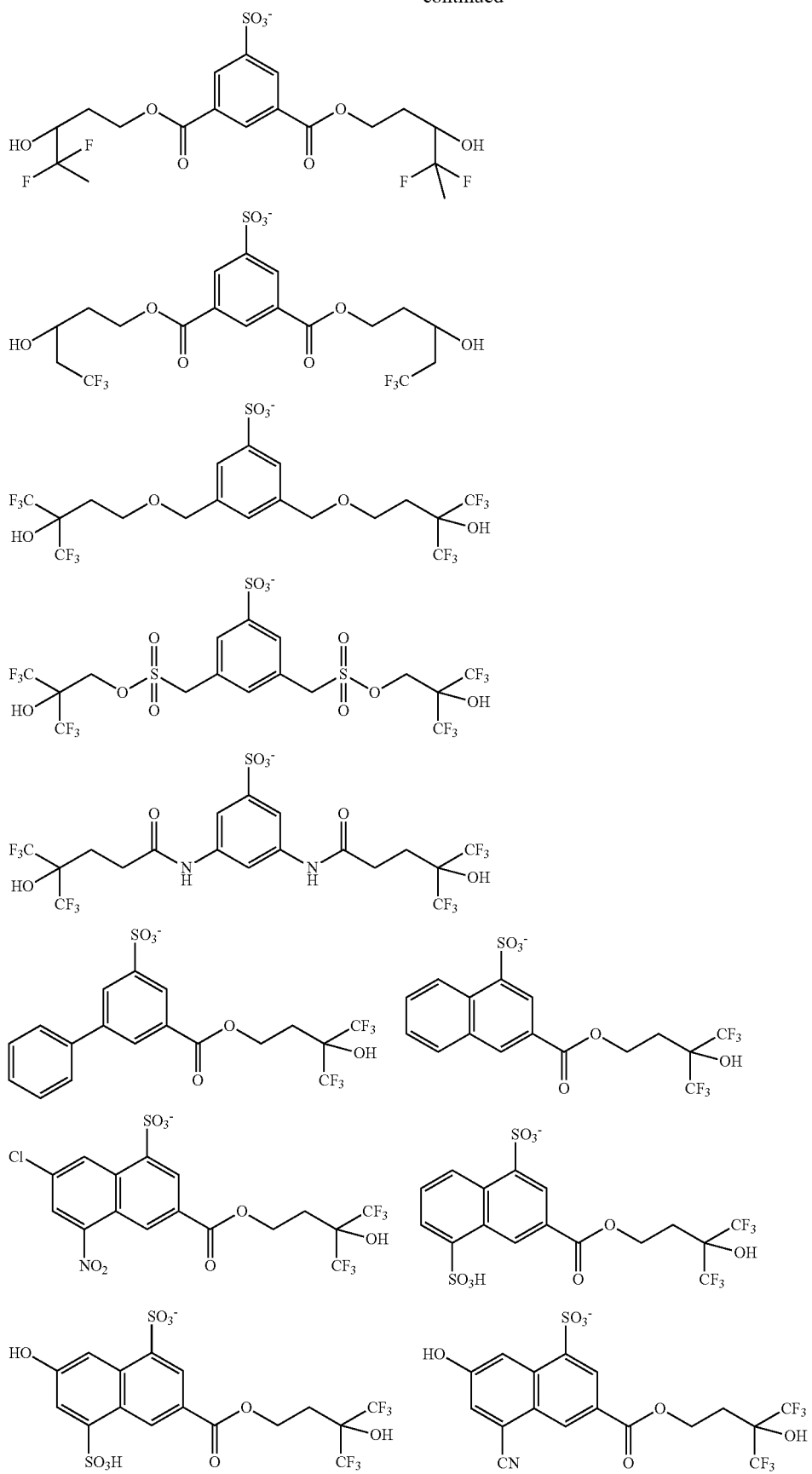

47                                              48
-continued
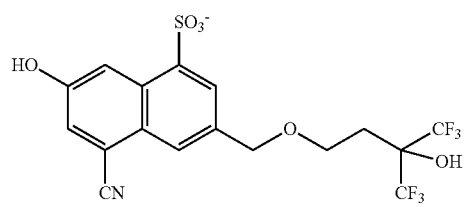
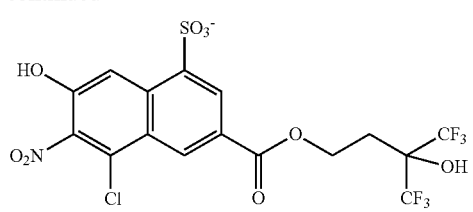
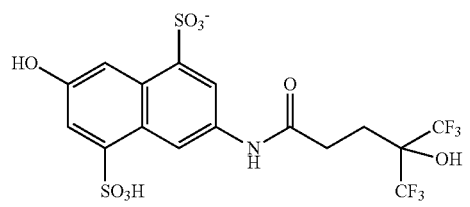
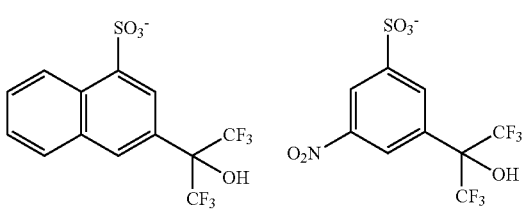
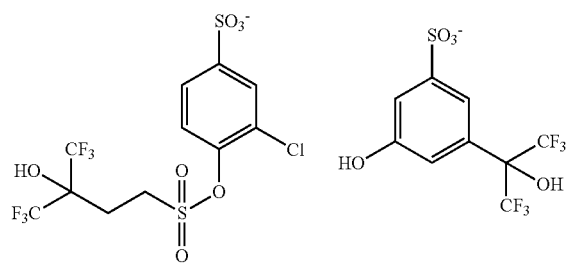
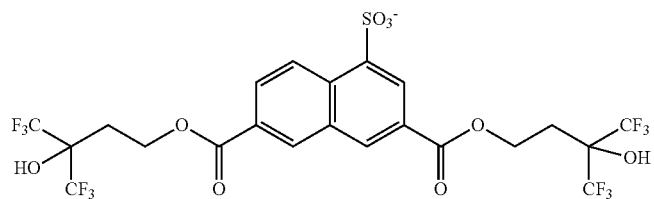
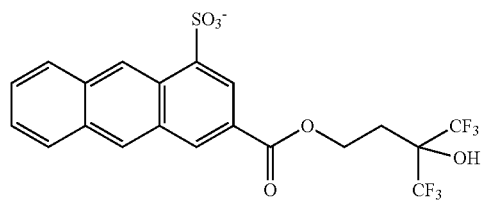
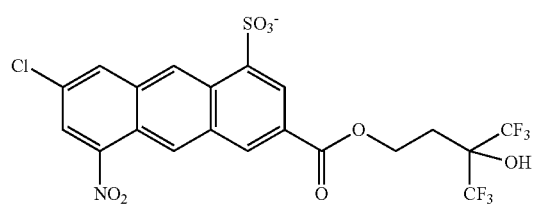
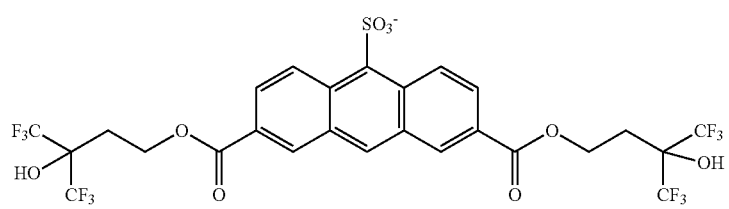
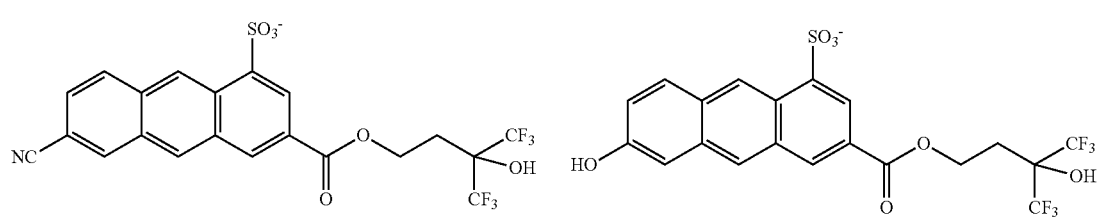

-continued
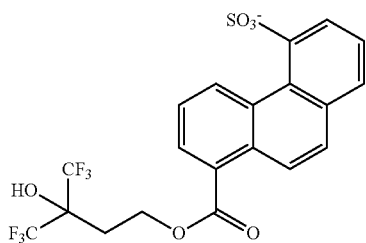 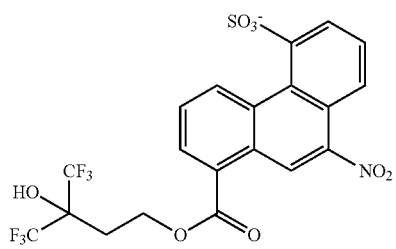
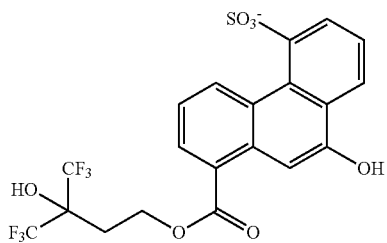 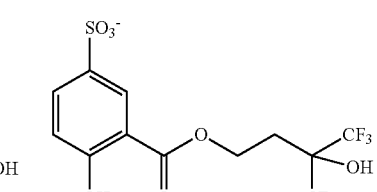 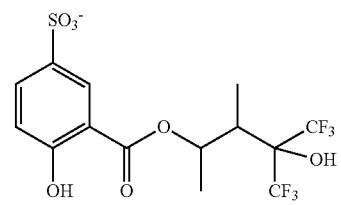
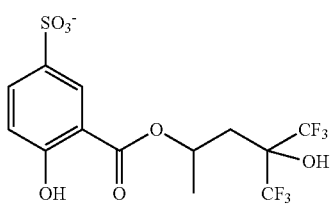 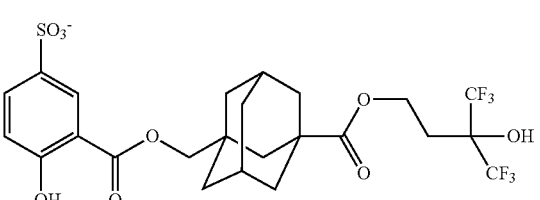
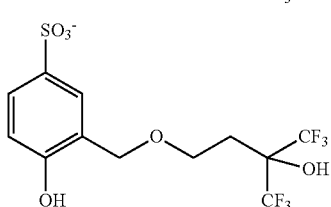 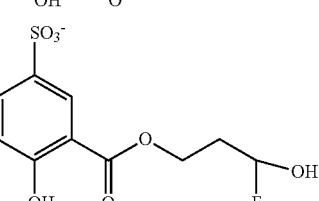 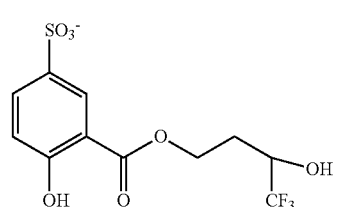
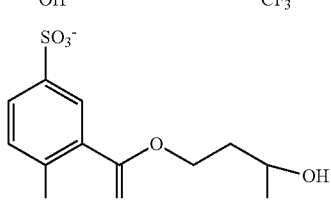 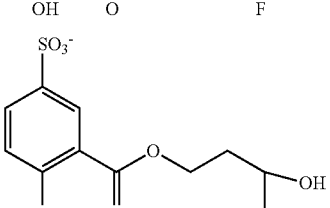 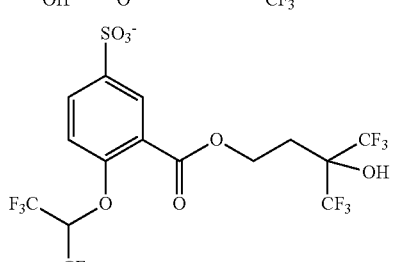
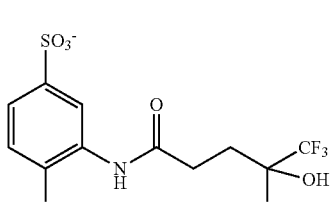 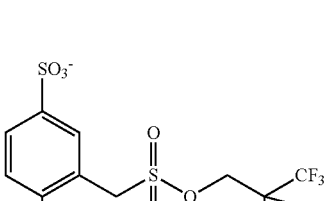 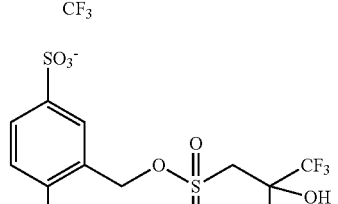
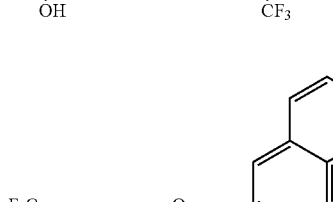 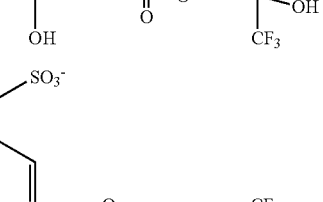 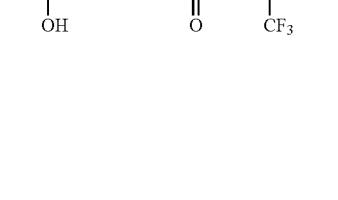
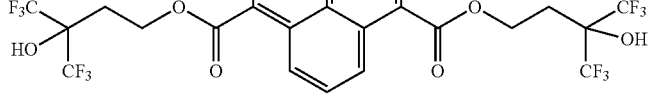

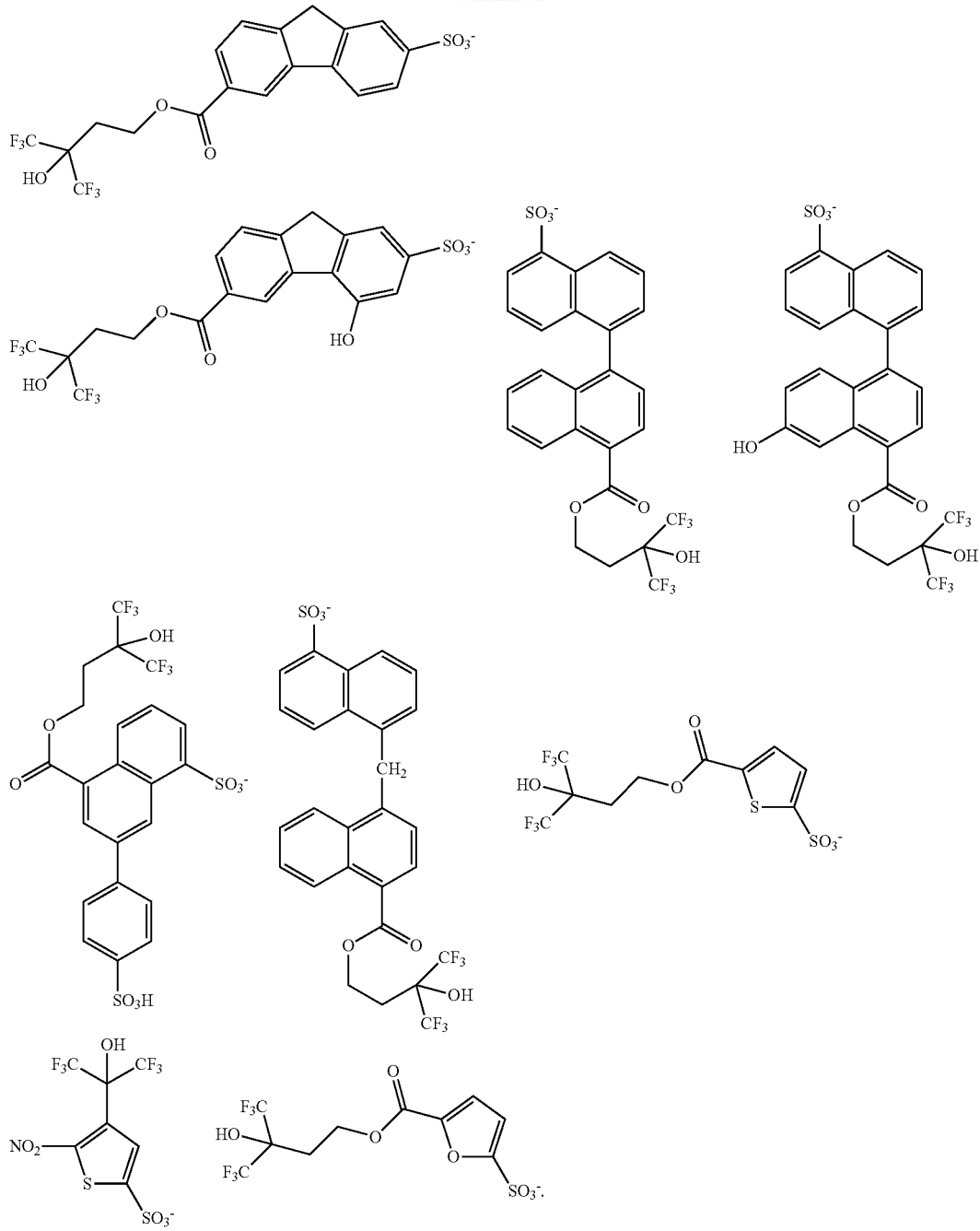

7. A photoresist pattern trimming composition, comprising: an ionic thermal acid generator of claim 1, a matrix polymer and a solvent.

8. The photoresist pattern trimming composition of claim 7, wherein the solvent is an organic solvent.

9. The photoresist pattern trimming composition of claim 7, wherein the anion comprises a plurality of fluorinated alcohol groups of the formula —C(CF$_3$)$_2$OH.

10. The photoresist pattern trimming composition of claim 7, wherein the fluorinated alcohol group is bonded to an aromatic ring of the anion through an ester group.

11. The photoresist pattern trimming composition of claim 7, wherein the thermal acid generator is of the following general formula (I):

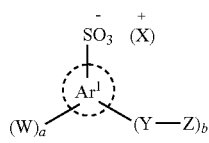

(I)

wherein: Ar¹ represents an optionally substituted carbocyclic or heterocyclic aromatic group; W independently represents a group chosen from carboxyl, hydroxy, nitro, cyano, C1-5 alkoxy and formyl; X is a cation; Y independently represents a linking group; Z independently represents a group chosen from hydroxyl, fluorinated alcohols, esters, optionally substituted alkyl, C5 or higher optionally substituted monocyclic, polycyclic, fused polycyclic cycloaliphatic, or aryl, which may optionally comprise a heteroatom, provided at least one occurrence of Z is a fluorinated alcohol group of the formula —C(CF$_3$)$_2$OH; a is an integer of 0 or greater; b is an integer of 1 or greater; provided that a+b is at least 1 and not greater than the total number of available aromatic carbon atoms of the aromatic group.

12. A method of trimming a photoresist pattern, comprising:
(a) providing a substrate;
(b) forming a photoresist pattern on the substrate, wherein the photoresist pattern is formed from a photoresist composition comprising: a matrix polymer comprising an acid labile group; a photoacid generator; and a solvent;
(c) coating a photoresist trimming composition of claim 8 on the substrate over the photoresist pattern;
(d) heating the coated substrate, thereby causing a change in polarity of the photoresist matrix polymer in a surface region of the photoresist pattern; and
(e) contacting the photoresist pattern with a rinsing agent to remove the surface region of the photoresist pattern, thereby forming a trimmed photoresist pattern.

13. The method of claim 12, wherein the anion comprises a plurality of fluorinated alcohol groups of the formula —C(CF$_3$)$_2$OH.

14. The method of claim 12, wherein the fluorinated alcohol group is bonded to an aromatic ring of the anion through an ester group.

15. The method of claim 12, wherein the thermal acid generator is of the following general formula (I):

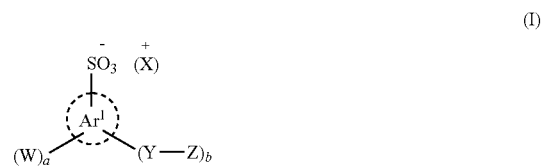

wherein: Ar¹ represents an optionally substituted carbocyclic or heterocyclic aromatic group; W independently represents a group chosen from carboxyl, hydroxy, nitro, cyano, C1-5 alkoxy and formyl; X is a cation; Y independently represents a linking group; Z independently represents a group chosen from hydroxyl, fluorinated alcohols, esters, optionally substituted alkyl, C5 or higher optionally substituted monocyclic, polycyclic, fused polycyclic cycloaliphatic, or aryl, which may optionally comprise a heteroatom, provided at least one occurrence of Z is a fluorinated alcohol group of the formula —C(CF$_3$)$_2$OH; a is an integer of 0 or greater; b is an integer of 1 or greater; provided that a+b is at least 1 and not greater than the total number of available aromatic carbon atoms of the aromatic group.

16. A photoresist pattern trimming composition, comprising: an ionic thermal acid generator of claim 5, a matrix polymer and a solvent.

17. The photoresist pattern trimming composition of claim 16, wherein the thermal acid generator anion is chosen from the following:

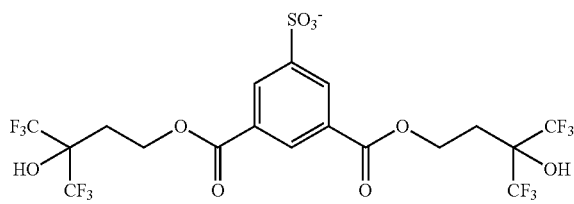

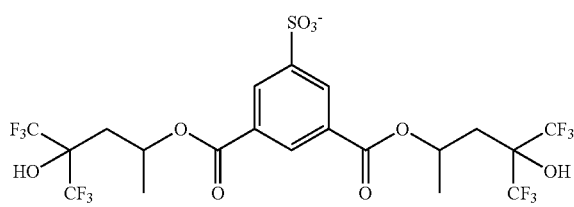

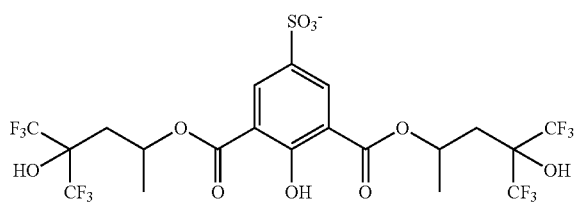

-continued
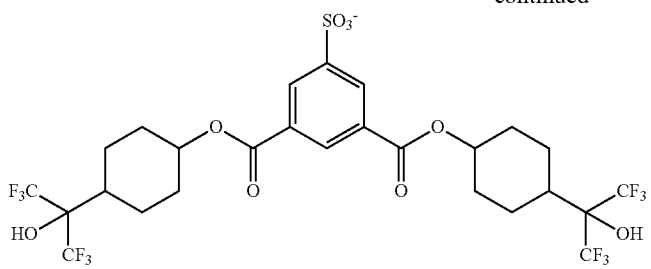
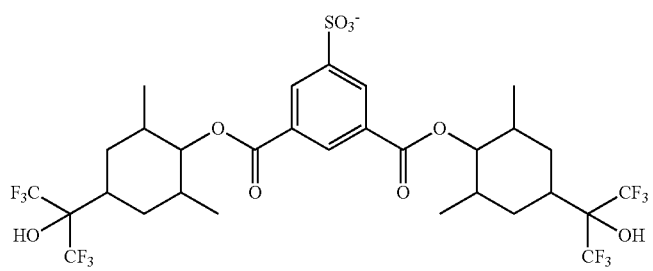
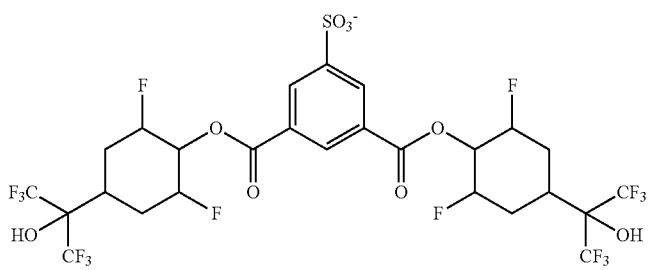
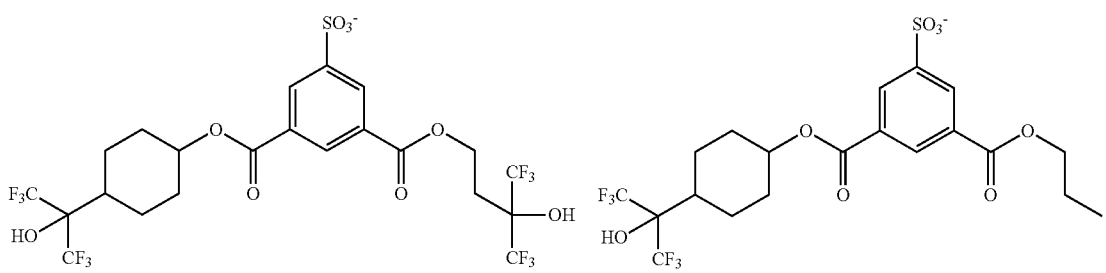
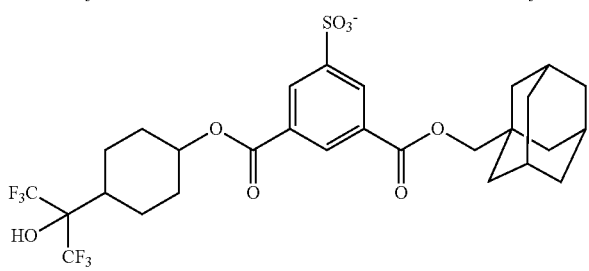
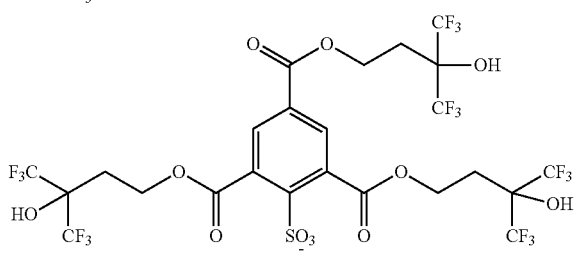

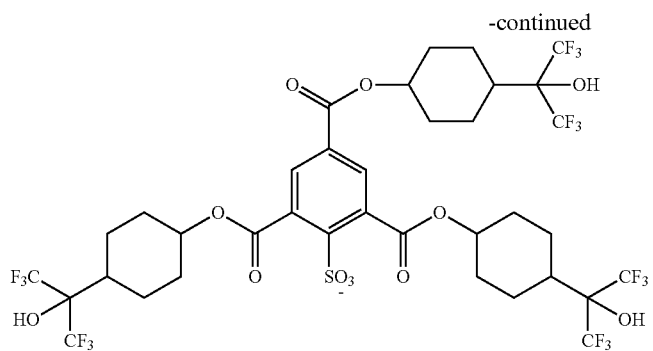
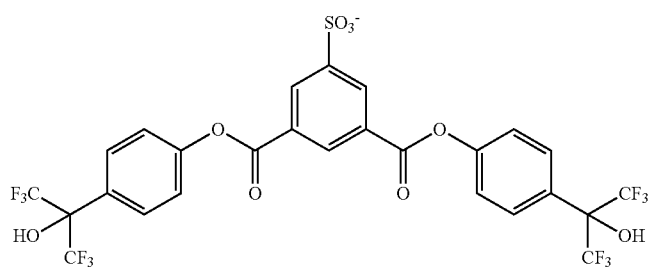
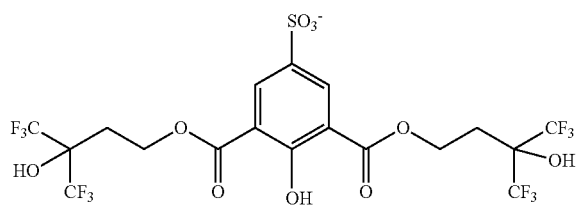
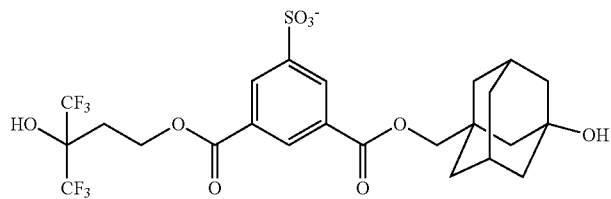
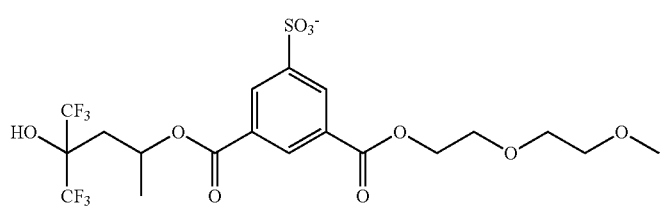
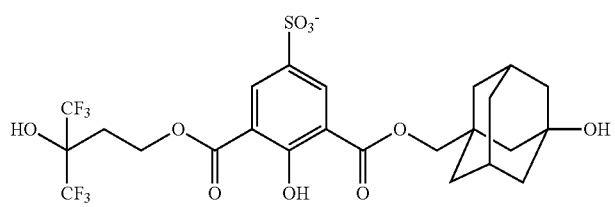
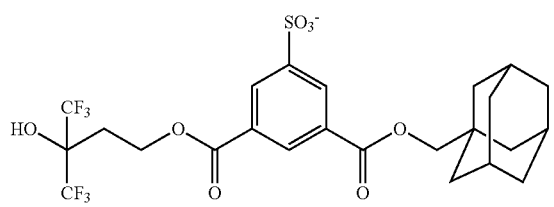

-continued
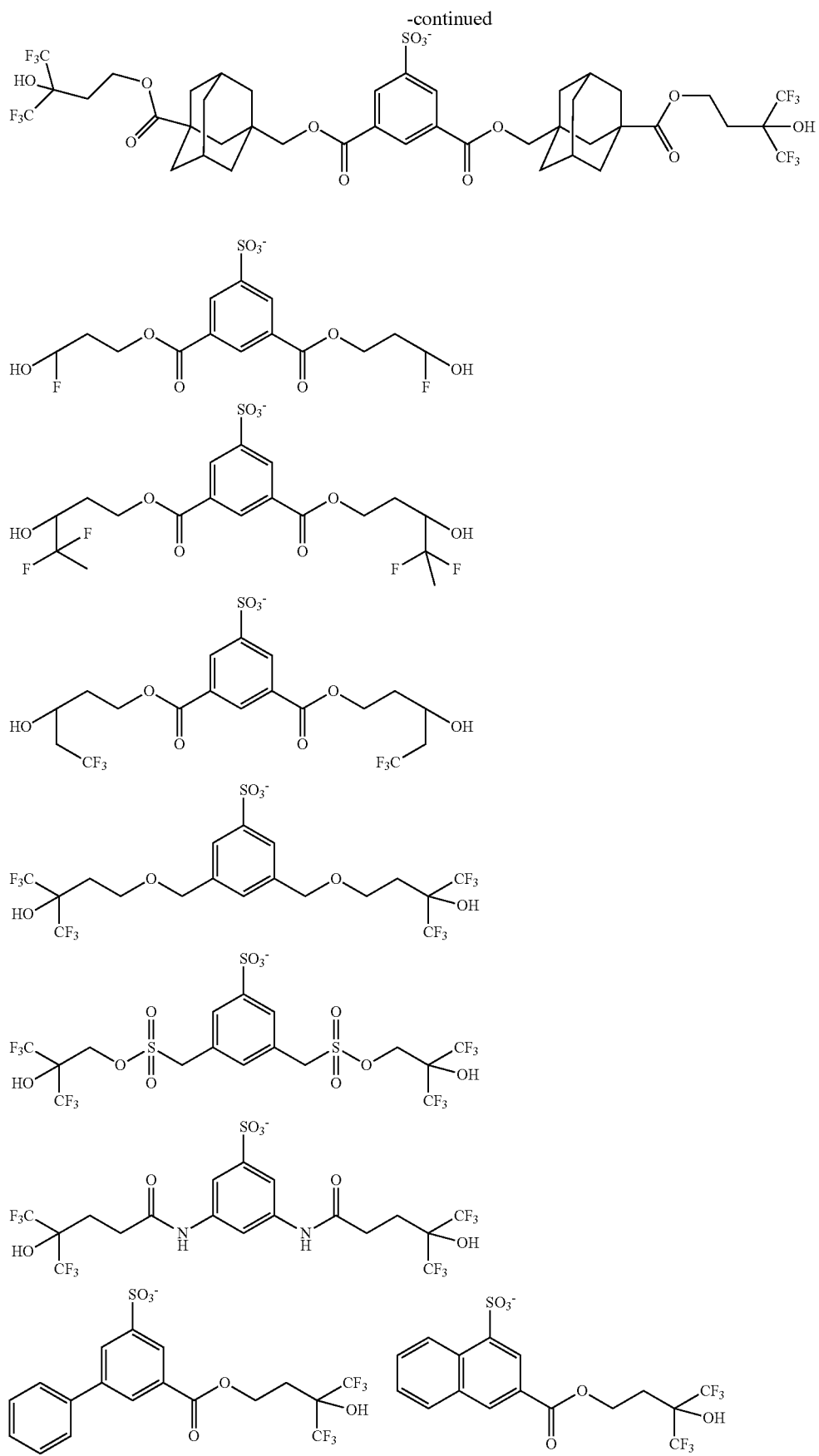

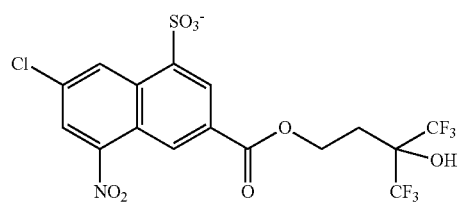
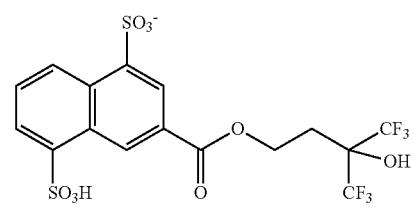
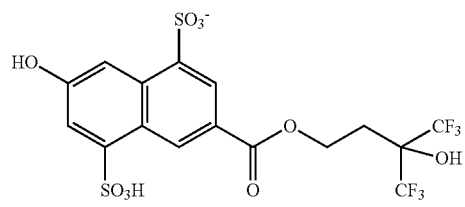
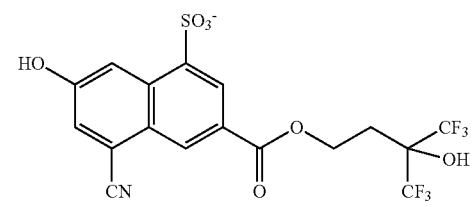
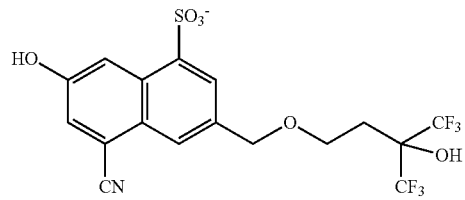
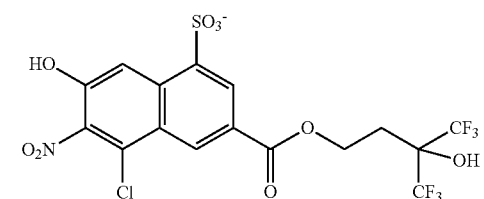
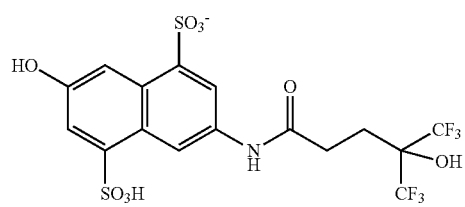
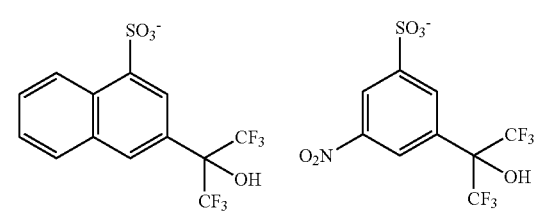
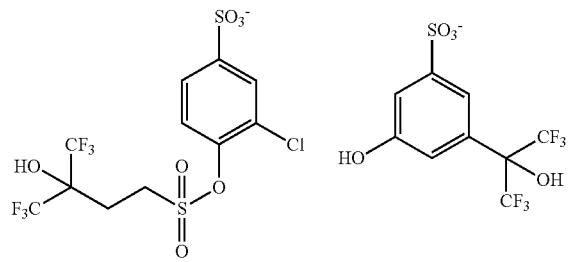
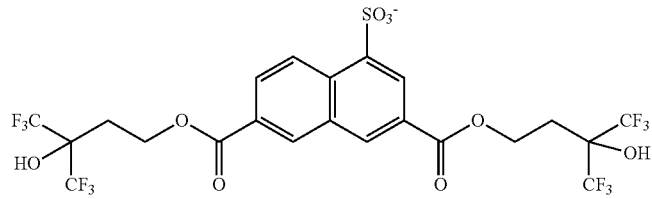
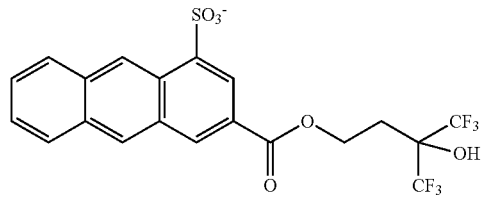
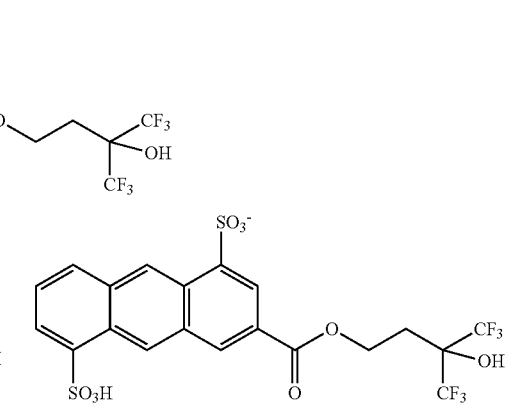
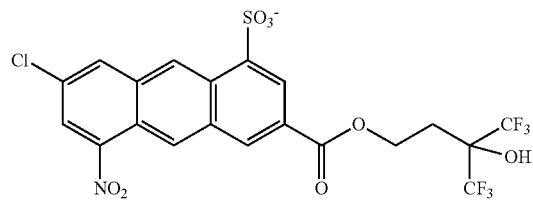

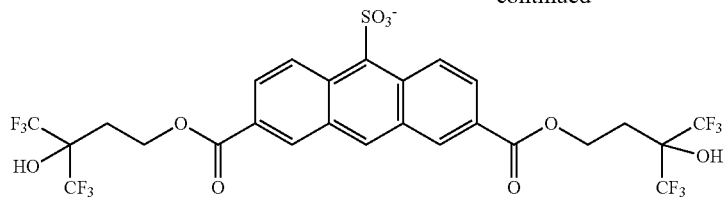
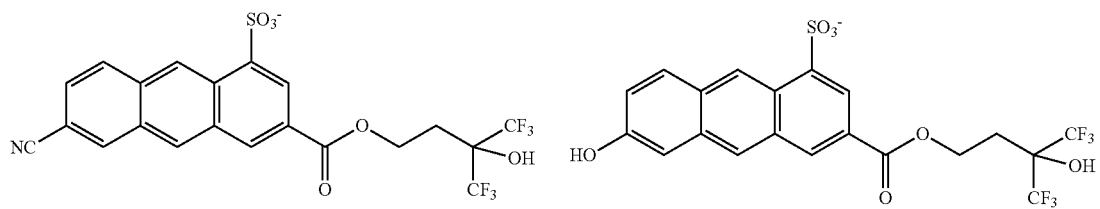
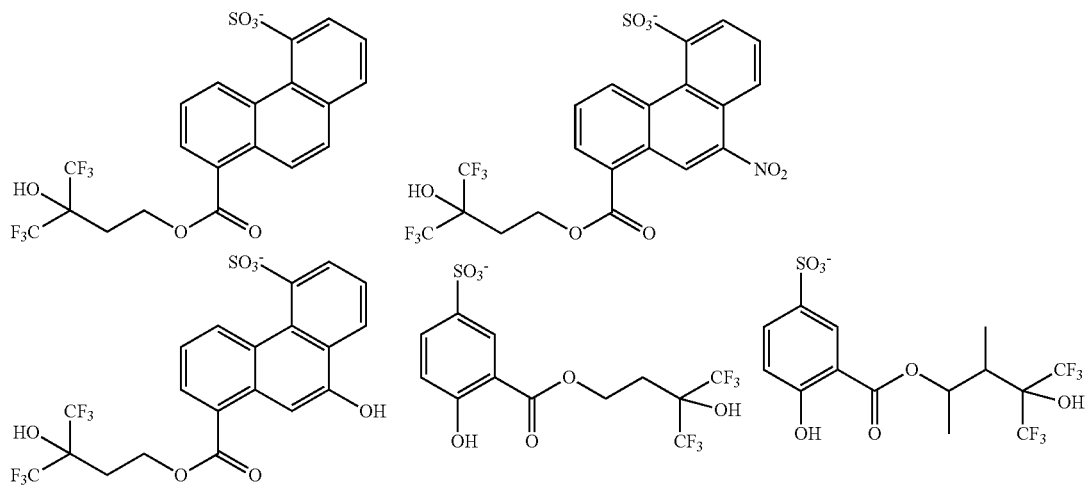
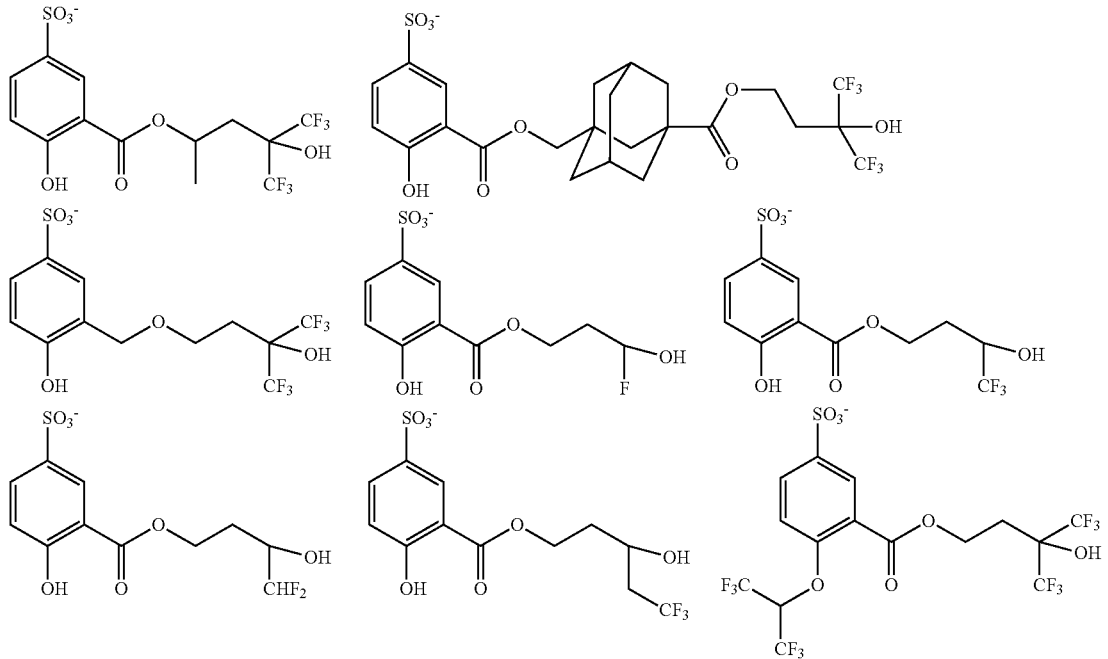

65 66
-continued
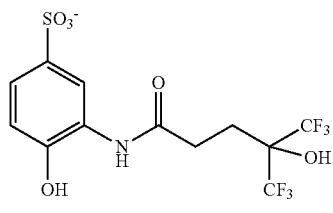
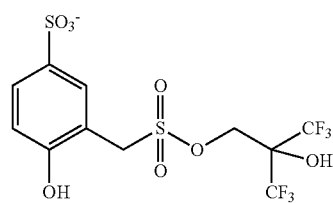
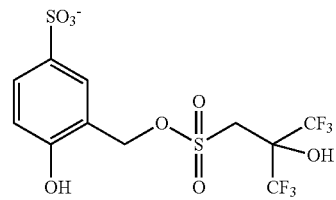
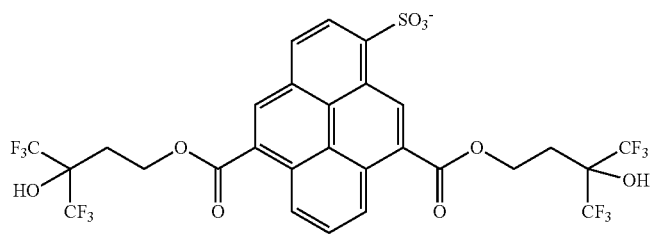
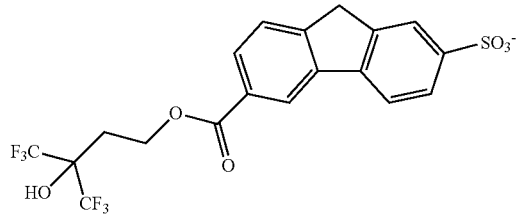
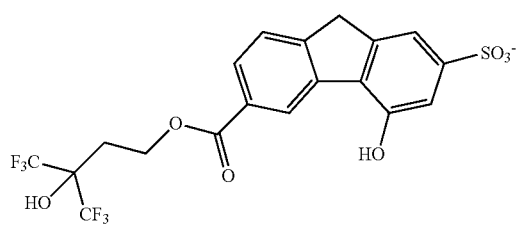
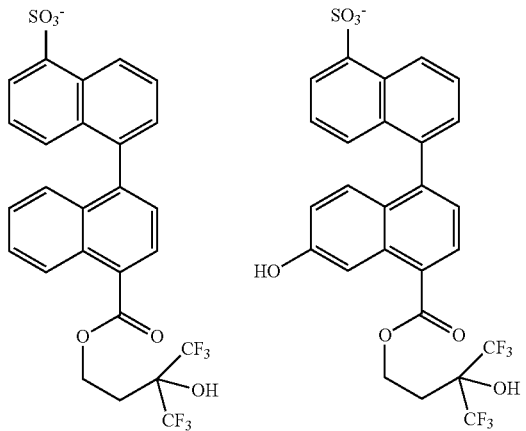
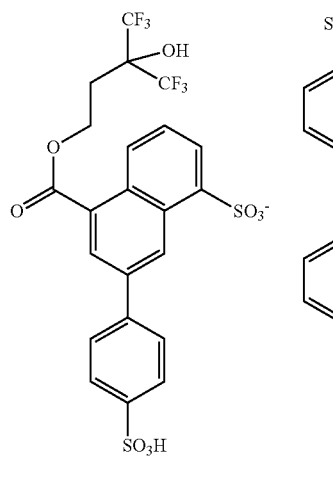
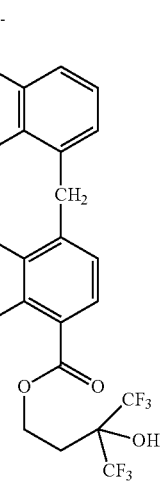
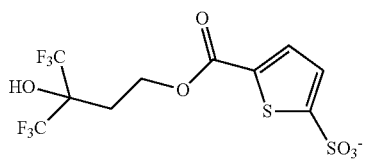

-continued

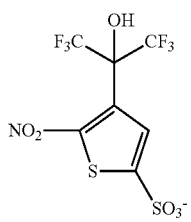 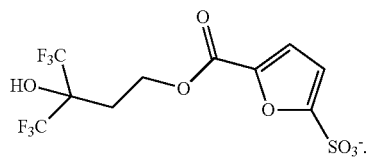

18. A method of trimming a photoresist pattern, comprising:
(a) providing a substrate;
(b) forming a photoresist pattern on the substrate, wherein the photoresist pattern is formed from a photoresist composition comprising: a matrix polymer comprising an acid labile group; a photoacid generator; and a solvent;
(c) coating a photoresist trimming composition of claim 16 on the substrate over the photoresist pattern;
(d) heating the coated substrate, thereby causing a change in polarity of the photoresist matrix polymer in a surface region of the photoresist pattern; and
(e) contacting the photoresist pattern with a rinsing agent to remove the surface region of the photoresist pattern, thereby forming a trimmed photoresist pattern.

* * * * *